United States Patent
Yamashita

(10) Patent No.: US 9,302,948 B2
(45) Date of Patent: Apr. 5, 2016

(54) FERTILIZER COMPOSITIONS COMPRISING A CELLULOSE NUTRIENT COMPONENT AND METHODS FOR USING SAME

(71) Applicant: Thomas T. Yamashita, Turlock, CA (US)

(72) Inventor: Thomas T. Yamashita, Turlock, CA (US)

(*) Notice: Subject to any disclaimer, the term of this patent is extended or adjusted under 35 U.S.C. 154(b) by 0 days.

(21) Appl. No.: 14/603,929

(22) Filed: Jan. 23, 2015

(65) Prior Publication Data

US 2015/0239788 A1    Aug. 27, 2015

Related U.S. Application Data

(60) Provisional application No. 61/943,947, filed on Feb. 24, 2014.

(51) Int. Cl.
| | |
|---|---|
| *C05B 17/00* | (2006.01) |
| *C05F 11/08* | (2006.01) |
| *A01N 63/00* | (2006.01) |
| *A01N 63/04* | (2006.01) |
| *C05G 3/02* | (2006.01) |

(52) U.S. Cl.
CPC ............... *C05B 17/00* (2013.01); *A01N 63/00* (2013.01); *A01N 63/04* (2013.01); *C05F 11/08* (2013.01); *C05G 3/02* (2013.01)

(58) Field of Classification Search
None
See application file for complete search history.

(56) References Cited

U.S. PATENT DOCUMENTS

| | | | |
|---|---|---|---|
| 4,229,442 | A | 10/1980 | Pinckard |
| 5,439,873 | A | 8/1995 | Kinnersley |
| 5,549,729 | A | 8/1996 | Yamashita |
| 5,582,627 | A | 12/1996 | Yamashita |
| 5,696,094 | A | 12/1997 | Yamashita |
| 5,749,935 | A | 5/1998 | Takehara et al. |
| 5,797,976 | A | 8/1998 | Yamashita |
| 6,165,245 | A | 12/2000 | Yamashita |
| 6,187,326 | B1 | 2/2001 | Yamashita |
| 6,241,795 | B1 | 6/2001 | Svec et al. |
| 6,309,440 | B1 | 10/2001 | Yamashita |
| 6,318,023 | B1 | 11/2001 | Yamashita |
| 6,336,772 | B1 | 1/2002 | Yamashita |
| 6,383,245 | B1 | 5/2002 | Yamashita |
| 6,475,258 | B1 | 11/2002 | Yamashita |
| 6,524,600 | B2 | 2/2003 | Yamashita |
| 6,871,446 | B1 | 3/2005 | Yamashita |
| 6,874,277 | B2 | 4/2005 | Yamashita |
| 6,953,585 | B2 | 10/2005 | Yamashita |
| 7,261,902 | B2 | 8/2007 | Yamashita |
| 7,501,006 | B2 | 3/2009 | Rogers et al. |
| 7,776,124 | B2 | 8/2010 | Binder et al. |
| 8,002,870 | B2 | 8/2011 | Yamashita |
| 8,337,583 | B2 | 12/2012 | Yamashita |
| 2005/0158355 | A1 | 7/2005 | Yamashita |
| 2005/0197252 | A1 | 9/2005 | Yamashita |
| 2006/0083725 | A1 | 4/2006 | Dean |
| 2011/0005960 | A1 | 1/2011 | Guha et al. |
| 2012/0285211 | A1 | 11/2012 | Kucera et al. |

FOREIGN PATENT DOCUMENTS

| | | |
|---|---|---|
| CN | 101096328 A | 1/2008 |
| CN | 103288548 A | 9/2013 |
| WO | WO9113844 | 9/1991 |
| WO | WO9203393 | 3/1992 |
| WO | WO9522900 | 8/1995 |
| WO | WO0063138 | 10/2000 |
| WO | WO2012063091 A1 | 5/2012 |

OTHER PUBLICATIONS

Badra et al., The relationship between phenolic content and *Tylenchulus semipenetrans* populations in nitrogen-amended citrus plants, Revue Nematol (1979), 2(2):161-164.
Chitwood, Phytochemical Based Strategies for Nematode Control, Annu Rev Phytopathol (2002), 40:221-249.
Kalaitzidis et al., Preliminary comparative analyses of two Greek leonardites, Fuel (2003), 82(7):859-861.
Mahajan et al., Nematicidal activity of some phenolic compounds against Meloidogyne incognita, Rev Nematol (1985), 8:161-164.
Nitao et al., In vitro assays of Meloidogyne incognita and Heterodera glycines for detection of nematode-antagonistic fungal compounds, J Nematol (1999), 31(2):172-183.
Ohri et al., Effect of phenolic compounds on nematodes—A review, J Appl Nat Sci (2010), 2(2):344-350.
Roy et al., Plant Nutrition for Food Security—A guide for integrated nutrient management, Food and Agriculture Organization of the United Nations—FAO Fertilizer and Plant Nutrition Bulletin 16, Rome, Italy, 2006.
Schafer et al., A calcium-channel homologue required for adaptation to dopamine and serotonin in Caenorhabditis elegans, Nature (1995), 375(6526):73-78.
Wu et al., Allelochemicals in wheat (*Triticum aestivum* L.): Cultivar differences in the exudation of phenolic acids, J Agric Food Chem (2001), 49(8):3742-3745.
Yohe, Binding Materials Used in Making Pellets and Briquets, Industrial Minerals Notes No. 19, Illinois State Geological Survey, Nov. 1964, 58 pages.
The Beginners Guide to Pellet Production, www.PelHeat.com, Accessed Dec. 3, 2013.

*Primary Examiner* — Wayne Langel
(74) *Attorney, Agent, or Firm* — Bret E. Field; Bozicevic, Field & Francis LLP

(57) ABSTRACT

Aspects of the invention include compositions for fertilizing and remediating soil. Compositions according to certain embodiments include a cellulose nutrient composition, a microbial blend composition, a source of nitrogen, a source of phosphorus and exotic micronutrients. Methods for using compositions of the invention to fertilize and remediate soil and kits having one or more compositions for fertilizing and remediating soil are also described.

20 Claims, No Drawings

FERTILIZER COMPOSITIONS COMPRISING A CELLULOSE NUTRIENT COMPONENT AND METHODS FOR USING SAME

CROSS-REFERENCE TO RELATED APPLICATIONS

This application is related to U.S. Provisional Patent Application Ser. No. 61/943,947, filed Feb. 24, 2014, the disclosure of which application is incorporated herein by reference.

INTRODUCTION

Fertilizers are organic or inorganic materials of natural or synthetic origin that are added to soil to supply one or more plant nutrients needed for plant nutrition. Fertilizers can come in various forms, such as granulated or powdered forms, liquid fertilizers including neat liquids and aqueous mixture, semi-solids as well as slurry suspensions and even in gaseous form. Accordingly, the nutrients from the fertilizer may be provided to the plant in varying ways, including absorption through the roots or plant foliage.

Commercially, fertilizers have been used to remediate soils either to correct natural deficiencies, replace missing components or to supplement essential nutrients present in low abundance. It is estimated that between 30% and 50% of all agricultural crop yield is attributed to benefits provided by fertilizers. In spite of the number of different fertilizers that have been developed, there is a continued need to develop new compositions.

SUMMARY

Aspects of the invention include compositions for fertilizing and remediating soil. Compositions according to certain embodiments include a cellulose nutrient component, a microbial blend component, a source of nitrogen, a source of phosphorus and exotic micronutrients. Methods for using compositions of the invention to remediate soil and kits having one or more of the subject compositions are also described.

In embodiments of the invention, compositions for fertilizing and remediating soil are provided and include a cellulose nutrient component, a microbial blend component, a source of nitrogen, a source of phosphorus and exotic micronutrients. In some instances, the cellulose nutrient component is a green manure crop. In other embodiments, the cellulose nutrient component is a dried manure crop. In some instances, the manure crop includes grass family plant tissue, such as from rice hulls, rice straw, wheat straw, sorghum sudan straw, barley straw, rye straw, oat straw, rye straw, corn straw, alfalfa hay, bentgrass hay, softwood sawdust, hardwood sawdust, sunflower seed shells, almond hulls, vetch hay, foxtail grass hay, beardgrass hay, whiskey grass hay, bluestem hay, signal grass, running grass, buffelgrass, lovegrass, bowgrass, hindigrass, bluegrass, crabgrass, couchgrass, barnyard grass, antelopegrass, cupgrass, whipgrass, cogongrass, centipedegrass, sesagrass, armgrass, panicgrass, witchgrass, sweetgrass, millet, torpedograss, ticklegrass, switchgrass, buffalograss, dallisgrass, paspalum, knotgrass, vaseygrass, pennisetum, itchgrass, pigeongrass, bristlegrass, Saint Augustine grass, tasselgrass, goatgrass, quackgrass, slender foxtail, windgrass, Downey Brome, fingergrass, rhodesgrass, bermudagrass, crowfoot grass, goosegrass, stinkgrass, velvetgrass, Hares Tall grass, canarygrass, smutgrass, wild garlic, nutsedge, clover, Johnsongrass, and walnut shells. For example, the cellulose nutrient component is, in certain instances, rice hulls. In these embodiments, the cellulose nutrient component may be a source of one or more of humic acid, fulvic acid and ulmic acid.

In embodiments, compositions also include a microbial blend component. In some instances, the microbial blend component may include one or more bacterial species and one or more fungal species. For example, the microbial blend component may, in certain instances, include at least five distinct microbial species, such as five distinct bacterial species. In other instances, the microbial blend component includes at least 2 distinct fungal species. In certain embodiments, the microbial blend component includes a bacterial species such as *Bacillus subtilis; Bacillus thuringiensis; Bacillus cereus; Bacillus megaterium; Bacillus penetrans; Arthrobacter paraffineus*; and *Pseudomonas fluorescens*. In other embodiments, the microbial blend includes a fungal species such as *Trichoderma viride, Trichoderma harzianum, Trichoderma polysporum, Trichoderma hamatum, Trichoderma koningii, Gliocladium virens, Gieocladium roseum, Gliocladium catenulatum, Penicillium oxalicum, Penicillium lilacinum, Penicillium nigricans, Penicillium chrysogenum* and *Penicillium frequentens*. In some embodiments, the microbial blend component further includes a carrier, such as a liquid or solid carrier. In embodiments of the invention, the microbial blend component includes microbial species capable of digesting the cellulose nutrient component. The microbial blend component may include one or more of a bacterial and fungal species that are soil-borne pathogen antagonist, such as a plant parasitic nematode antagonist. For example, the microbial blend composition may include rhizobacteria.

In embodiments, compositions also include exotic micronutrients. For example, the exotic micronutrients may be one or more (e.g., 10 or more) of Aluminum (Al), Antimony (Sb), Barium (Ba), Beryllium (Be), Bismuth (Bi), Boron (B), Bromine (Br), Cadmium (Cd), Cerium (Ce), Cesium (Cs), Chromium (Cr), Cobalt (Co), Dysprosium (Dy), Erbium (Er), Europium (Eu), Fluorine (F), Gadolinium (Gd), Gallium (Ga), Germanium (Ge), Gold (Au), Hafnium (Hf), Holmium (Ho), Indium (In), Lanthanum (La), Lutetium (Lu), Lithium (Li), Mercury (Hg), Molybdenum (Mo), Neodymium (Nd), Nickel (Ni), Niobium (Nb), Platinum (Pt), Praseodymium (Pr), Rhodium (Rh), Ruthenium (Ru), Samarium (Sm), Scandium (Sc), Selenium (Se), Silicon (Si), Silver (Ag), Strontium (Sr), Sulfur (S), Tellurium (Te), Terbium (Tb), Thallium (Tl), Thorium (Th), Thulium (Tm), Tin (Sn), Titanium (Ti), Tungsten (W), Vanadium (V), Ytterbium (Yb), Yttrium (Y), and Zirconium (Zr).

Compositions may also include one or more of an activator composition, a carbon skeleton energy component, macronutrients, micronutrients, vitamin cofactors, a complexing agent, an ionophore. In certain instances, the composition further includes wood, such as wood shaving dust or pine resin.

In certain embodiments, compositions are baled or pelletized. In these embodiments, the composition may further include a binder, such as calcium lignosulfate. For example, compositions of the invention are, in certain instances, pelletized compositions having a cellulose nutrient component, a microbial blend component, a source of nitrogen, a source of phosphorus, exotic micronutrients, a binder and an activator composition. In other instances, compositions are pelletized compositions having a cellulose nutrient component, a microbial blend component, a source of nitrogen, a source of phosphorus, exotic micronutrients, binder, wood and an activator composition. In yet other instances, compositions are pelletized compositions having a cellulose nutrient component, a microbial blend component, a source of nitrogen, a source of phosphorus, exotic micronutrients, a binder, an activator composition and one or more of a carbon skeleton energy component, macronutrients, micronutrients, vitamin cofactors, a complexing agent, an ionophore. In still other instances, compositions are pelletized compositions having a cellulose nutrient component, a microbial blend component, a source of nitrogen, a source of phosphorus, exotic micronutrients, binder, wood, an activator composition and one or more of a carbon skeleton energy component, macronutrients, micronutrients, vitamin cofactors, a complexing agent, an ionophore.

In embodiments of the present invention, the subject compositions are synergistically effective combinations of a cellulose nutrient component, a microblend component, a source of nitrogen, a source of phosphorus and exotic micronutrients. The term "synergistically effective" means that compositions having a cellulose nutrient component, a microbial blend component, a source of nitrogen, a source of phosphorus and exotic micronutrients produces an effect (i.e., enhances soil fertilization and remediation) which is greater than would be achieved by the sum of each individual component. For example, a composition having a cellulose nutrient component, a microbial blend component, a source of nitrogen, a source of phosphorus and exotic micronutrients produces an effect that is 1% greater or more than would be achieved by the sum of the components of the composition, individually, such as 5% greater or more, such as 10% greater or more, such as 20% greater or more, such as 30% greater or more, such as 40% greater or more, such as 50% greater or more, such as 60% greater or more, such as 70% greater or more, such as 80% greater or more, such as 90% greater and including 100% greater or more. In certain instances, synergistic combinations of the present invention produce an effect which is 2-fold or greater, such as 5-fold or greater, such as 10-fold or greater and including 25-fold or greater than would be achieved by the sum of each component of the composition individually.

Aspects of the invention also include methods for using the subject compositions to fertilize and remediate soil. In some embodiments, methods include administering the composition to the top soil by a hand-held applicator or by ground-level mechanical machinery. In other embodiments, methods include administering the composition to the top soil by aircraft (e.g., helicopter, airplane). In yet other embodiments, methods include mixing the subject compositions with soil and applying the composition-soil mixture to the soil.

Aspects of the invention also include methods for evaluating the effect of the composition on the microbial population in the soil. In some embodiments, methods include administering the subject compositions to the soil and evaluating the population of microbial species present in the soil contacted with the subject compositions. In certain instances, evaluating the population of microbial species present in the soil contacted with the subject composition includes detecting metabolic activity of microbial species in the soil. For example, detecting metabolic activity may include subjecting a soil sample contacted with the subject composition to a formazan test. In certain embodiments, methods also include evaluating the overall health of one or more plants in the soil contacted with the subject compositions.

Aspects of the invention also include methods for preparing pelletized fertilizer compositions. In some embodiments, the methods include processing a cellulose nutrient component into a powder; contacting the powdered cellulose nutrient composition with a microbial blend component, a source of nitrogen, a source of phosphorus and exotic micronutrients to produce a fertilizer precursor composition and pelletizing the fertilizer precursor composition with a binder to produce fertilizer pellets. In certain instances, methods also include pelletizing the fertilizer precursor composition with wood, such as wood shaving dust or pine resin.

Applications for the subject composition include increasing the microbial activity of the soil, remediating soil containing one or more plant toxic compounds present in the soil, improving the overall nutrient content of the soil, reducing the overall negative effects of plant parasitic species present in the soil, increasing the overall production of crops present in the soil contacted with the subject composition, and the like.

DETAILED DESCRIPTION

Aspects of the invention include compositions for fertilizing and remediating soil. Compositions according to certain embodiments include a cellulose nutrient component, a microbial blend component, a source of nitrogen, a source of phosphorus and exotic micronutrients. Methods for using compositions of the invention to fertilize and remediate soil and kits having one or more of the subject compositions are also described.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

As reviewed above, the present invention provides compositions for fertilizing and remediating soil. In further describing embodiments of the invention, compositions having a cellulose nutrient component, a microbial blend component, a source of nitrogen, a source of phosphorus and exotic micronutrients are first reviewed in greater detail. Next, methods for using the subject compositions to remediate and fertilize soil and methods for evaluating the effect of the subject composition on soil microbial activity and the overall health of the subject plants present in the soil contacted with the subject compositions are described. Kits including one or more of the subject compositions are also described.

Compositions for Fertilizing and Remediating Soil

As summarized above, the subject invention provides compositions for fertilizing and remediating soil. The term "fertilizing" is used herein in its conventional sense to refer to providing or supplementing essential nutrients in the soil. Fertilizing may be passive, such as where the subject compositions simply provide a source of essential nutrients to the soil. Alternatively, fertilizing may be active, such as where the subject composition initiates, catalyzes or otherwise facilitates uptake of the essential nutrients by plants in the soil. In certain embodiments, fertilizing the soil may be realized by an enhancement in the overall health of plants in soil contacted with the subject composition, where in some instances the desired enhancement ultimately results in greater production of some desirable parameter, such as for example the amount of harvestable crop produced.

For example, in some embodiments enhanced overall health of plants in soil treated with compositions of interest includes an increased amount of harvested crop by 10% or more, such as 25% or more, such as 50% or more, such as 75% or more and including increasing the amount of harvested crop by 100% or more. For example, the increased amount of harvested crop may range from 10% to 100%, such as from 25% to 75% and including from 30% to 60%. In other instances, compositions of interest may increase harvested crop production by 1.5-fold or greater, such as 2-fold or greater, such as 2.5-fold or greater, such as 3-fold or greater, such as 5-fold or greater and including increasing harvested crop by 10-fold or greater. For example, the increased harvested crop may range from 1.5-fold to 25-fold, such as from 2-fold to 20-fold, such as from 3-fold to 18-fold and including from 5-fold to 15-fold. The above values are provided in comparison to a suitable control.

In certain instances, where the harvested crops are fruits or nuts, compositions for fertilizing soil provided by the invention may increase the amount of crop produced by 250 pounds per acre or more, such as 500 pounds per acre or more, such as 1000 pounds per acre or more, such as 1500 pounds per acre or more and including by 2000 pounds per acre or more, e.g., as compared to suitable control or reference (such where the subject compositions are not employed but all other parameters are the same). For example the harvested crop may be increased from 250 pounds to 5000 pounds, such as from 500 pounds to 4500 pounds, such as from 750 pounds to 4000 pounds and including from 1000 pounds to 3000 pounds. The above values are provided in comparison to a suitable control.

In other embodiments, enhanced overall health of the subject plants by fertilizing soil with compositions of interest is realized by an improvement in the quality of harvested crops (e.g., color, taste, duration of shelf life, etc.) as compared to harvested crops planted in soil not treated with the subject compositions.

Aspects of the invention also include compositions for remediating soil. The term "remediating" is used herein in its conventional sense to refer to reducing the overall negative effect of undesirable organic or inorganic contaminants in the soil on plants such that the plants experience a decreased amount of negative effects by the undesirable organic or inorganic contaminants as compared to plants in soil not treated with the subject composition. The overall negative effect by undesirable organic or inorganic contaminants may be reduced, such as by reducing the overall amount of undesirable organic or inorganic contaminants in the soil or by reducing the severity or extent of negative effects of the undesirable organic or inorganic contaminants (i.e., the amount of contaminants remain unchanged but initiate fewer detrimental effects).

As described in greater detail below, in some instances the subject compositions remediate soil by reducing or eliminating the overall negative effect of undesirable contaminants in the soil. In some embodiments, a reduction in the overall negative effect of undesirable contaminants may be a reduced severity or extent of damage by soil-borne pathogens. Compositions of the invention may, in certain instances, reduce the severity or extent of damage by soil-borne pathogens by decreasing the proliferation or density of soil-borne pathogens present in soil contacted with the subject compositions.

In other embodiments, a reduction in the overall negative effect of undesirable contaminants may be eliminating toxic organic or inorganic compounds present in the soil. Compositions may in some embodiments, eliminate toxic organic or inorganic compounds by oxidative-reduction reactions to decompose or degrade toxic compounds present in the soil. In other embodiments, compositions of interest eliminate toxic organic or inorganic compounds by enzymatic degradation. In yet other embodiments, compositions eliminate toxic organic or inorganic compounds through bioremediation by the one or more species present in the microbial blend component.

In embodiments of the present invention, the subject compositions are synergistically effective combinations of a cellulose nutrient component, a microbial blend component, a source of nitrogen, a source of phosphorus and exotic micronutrients. The term "synergistically effective" means that compositions having a combination of a cellulose nutrient component, a microbial blend component, a source of nitrogen, a source of phosphorus and exotic micronutrients produces an effect (i.e., enhances soil fertilization and remediation) which is greater than would be achieved by the sum of each individual component. For example, in some instances, the subject compositions produce an effect which is greater than would be achieved by the sum of individually applying a composition having a cellulose nutrient component and a composition having a microbial blend component, a source of nitrogen, a source of phosphorus and exotic micronutrients. In other instances, the subject compositions produce an effect which is greater than would be achieved by the sum of individually applying a composition having a microbial blend component and a composition having a cellulose nutrient component, a source of nitrogen, a source of phosphorus and exotic micronutrients. In yet other instances, the subject compositions produce an effect which is greater than would be achieved by the sum of individually applying a composition having a cellulose nutrient component and a microbial blend component and a composition having a source of nitrogen, a source of phosphorus and exotic micronutrients.

In embodiments of the present disclosure, a composition having a cellulose nutrient component, a microbial blend component, a source of nitrogen, a source of phosphorus and exotic micronutrients produces an effect that is 1% greater or more than would be achieved by the sum of the components of the composition, individually, such as 5% greater or more, such as 10% greater or more, such as 20% greater or more, such as 30% greater or more, such as 40% greater or more, such as 50% greater or more, such as 60% greater or more, such as 70% greater or more, such as 80% greater or more, such as 90% greater and including 100% greater or more. In certain instances, synergistic combinations of the present invention produce an effect which is 2-fold or greater, such as 5-fold or greater, such as 10-fold or greater and including 25-fold or greater than would be achieved by the sum of each component of the composition individually.

The synergistic effect may be realized, in certain embodiments, by increased soil fertilization as compared soil fertilization achieved by the sum of each component, individually. As discussed above, enhanced fertilization may be realized by greater production of some desirable parameter, such as for example the amount of harvestable crop produced. Likewise, the synergistic effect may be realized, in some embodiments, by increased soil remediation as compared to soil remediation by the sum of each component, individually. For example, increased soil remediation may be realized by a reduced overall negative effect of undesirable organic or inorganic contaminants in the soil on plants, such as by reducing the overall amount of undesirable organic or inorganic contaminants in the soil or by reducing the severity or extent of negative effects of the undesirable organic or inorganic contaminants.

In certain embodiments, the subject compositions are pelletized. The term "pelletized" is used herein in its conventional sense to refer to the process of compressing, molding, or otherwise shaping a composition having one or more components into the shape of pellet. Pelletized compositions of interest may include any combination of components, as described in greater detail below. For example, compositions of the invention are, in certain instances, pelletized compositions having a cellulose nutrient component, a microbial blend component, a source of nitrogen, a source of phosphorus, exotic micronutrients, a binder and an activator composition. In other instances, compositions are pelletized compositions having a cellulose nutrient component, a microbial blend component, a source of nitrogen, a source of phosphorus, exotic micronutrients, binder, wood and an activator composition. In yet other instances, compositions are pelletized compositions having a cellulose nutrient component, a microbial blend component, a source of nitrogen, a source of phosphorus, exotic micronutrients, a binder, an activator composition and one or more of a carbon skeleton energy component, macronutrients, micronutrients, vitamin cofactors, a complexing agent, an ionophore. In still other instances, compositions are pelletized compositions having a cellulose nutrient component, a microbial blend component, a source of nitrogen, a source of phosphorus, exotic micronutrients, binder, wood, an activator composition and one or more of a carbon skeleton energy component, macronutrients, micronutrients, vitamin cofactors, a complexing agent, an ionophore.

Pelletized compositions may take any desired shape, such as a disc, oval, half-circle, crescent-shaped, start shaped, square, triangle, rhomboid, pentagon, hexagon, heptagon, octagon, rectangle or other suitable polygon or may take the shape of a sphere, tablet, capsule, cube, cone, half sphere, star, triangular prism, rectangular prism, hexagonal prism or other suitable polyhedron. In certain embodiments, pelletized compositions of interest are spheroidal. In other embodiments, pelletized compositions are tablets. In yet other embodiments, pelletized compositions are cylindrical.

The size of pelletized compositions may also vary, in embodiments having a surface area which is 0.01 $cm^2$ or more, such as 0.05 $cm^2$ or more, such as 0.1 $cm^2$ or more, such as 0.5 $cm^2$ or more, such as 1 $cm^2$ or more, such as 2.5 $cm^2$ or more, such as 5 $cm^2$ or more, such as 7.5 $cm^2$ or more, such as 10 $cm^2$ or more, such as 12.5 $cm^2$ or more, such as 25 $cm^2$ or more and including 50 $cm^2$ or more. For example, the surface area of the subject pelletized composition may range from 0.01 $cm^2$ to 100 $cm^2$, such as 0.05 $cm^2$ to 90 $cm^2$, such as 0.1 $cm^2$ to 75 $cm^2$, such as 0.5 $cm^2$ to 50 $cm^2$, such as 0.75 $cm^2$ to 25 $cm^2$ and including 1 $cm^2$ to 10 $cm^2$. The volume of pelletized compositions of interest range from 0.01 $cm^3$ or more, such as 0.05 $cm^3$ or more, such as 0.1 $cm^3$ or more, such as 0.5 $cm^3$ or more, such as 1 $cm^3$ or more, such as 2.5 $cm^3$ or more, such as 5 $cm^3$ or more, such as 7.5 $cm^3$ or more, such as 10 $cm^3$ or more, such as 12.5 $cm^3$ or more, such as 25 $cm^3$ or more and including 50 $cm^3$ or more. For example, the volume of the subject pelletized composition may range from 0.01 $cm^3$ to 100 $cm^3$, such as 0.05 $cm^3$ to 90 $cm^3$, such as 0.1 $cm^3$ to 75 $cm^3$, such as 0.5 $cm^3$ to 50 $cm^3$, such as 0.75 $cm^3$ to 25 $cm^3$ and including 1 $cm^3$ to 10 $cm^3$.

In certain embodiments, compositions of interest are dry. By "dry" is meant that the subject compositions contain little to no water. Accordingly, in these embodiments compositions of interest are formulations which include 1% w/w water or less, such as 0.5% w/w water or less, such as 0.25% w/w water or less, such as 0.1% w/w water or less, such as 0.05% w/w water or less, such as 0.01% w/w water or less and including 0.001% w/w water or less. As such, compositions of the invention are solid compositions and may be provided in granular or powder form. Depending on the type of target plants and whether the composition will be applied to the foliage or soil, the size of particles of the compositions varies ranging from 0.01 μm to 100 μm, such as from 0.1 μm to 75 μm, such as from 1 μm to 50 μm, such as from 2.5 μm to 25 μm and including from 5 μm to 10 μm. In certain embodiments, compositions include granules which all have the same size (i.e., are monodisperse or uniform). In other embodiments, compositions include granules which have varying sizes (i.e., are polydisperse).

As summarized above, compositions of interest are compositions for fertilizing and remediating soil and include a cellulose nutrient component, a microbial blend component, a source of nitrogen, a source of phosphorus and exotic micronutrients. The subject compositions may also include one or more of a carbon skeleton energy component, macronutrients, micronutrients, vitamin cofactors, a complexing agent, an ionophore, a binder and an activator composition. The compositions are not naturally occurring, i.e., they are synthetic or man-made. Each of the different components of the compositions is now reviewed in greater detail. The amount of each component may vary in the subject compositions depending on the condition of the soil, geographical area and environmental conditions (e.g., wind conditions, precipitation, etc.) or application method employed. As such, the amounts of each component may be varied as desired, such as by increasing or reducing the amount or ratio of a particular component in the composition prior to application.

Cellulose Nutrient Component

In embodiments of the invention, compositions of interest include a cellulose nutrient component. The term "cellulose" is used herein in its conventional sense to refer to the polysaccharide composed of a linear or branched chain of β(1→4) linked D-glucose units bound together by glycosidic linkages, generally found as a structural component of primary cell walls of green plants, algae and oomycetes. Cellulose nutrient components of interest include both cellulose-containing compounds as well as hemicellulose-containing compounds. Depending on the type of target soil and accompanying microbial blend composition (as described in greater detail below), cellulose in the subject cellulose nutrient component may have any degree or polymerization (i.e., long-chain or short chain), such as for example cellulose having from 50 glucose monomers to 10,000 or more glucose monomers, such as 100 to 9000 glucose monomers, such as 150 to 5000 glucose monomers, such as 200 to 2500 glucose monomers and including from 400 to 1750 glucose monomers. As such, the molecular weight of cellulose in the subject cellulose nutrient composition may range, such as from 0.001 kDa to $10^6$ kDa, such as from 0.01 kDa to $10^5$ kDa, such as from 0.1 kDa to $10^4$ kDa and including from 1 kDa to $10^3$ kDa.

In some instances, the cellulose nutrient component includes plant tissue, such as tissue from plants of the grass family, including but not limited to, rice hulls, rice straw, wheat straw, sorghum sudan straw, barley straw, rye straw, oat straw, rye straw, corn straw, alfalfa hay, bentgrass hay, softwood sawdust, hardwood sawdust, sunflower seed shells, almond hulls, vetch hay, foxtail grass hay, beardgrass hay, whiskey grass hay, bluestem hay, signal grass, running grass, buffelgrass, lovegrass, bowgrass, hindigrass, bluegrass, crabgrass, couchgrass, barnyard grass, antelopegrass, cupgrass, whipgrass, cogongrass, centipedegrass, sesagrass, armgrass, panicgrass, witchgrass, sweetgrass, millet, torpedograss, ticklegrass, switchgrass, buffalograss, dallisgrass, paspalum, knotgrass, vaseygrass, pennisetum, itchgrass, pigeongrass, bristlegrass, Saint Augustine grass, tasselgrass, goatgrass, quackgrass, slender foxtail, windgrass, Downey Brome, fingergrass, rhodesgrass, bermudagrass, crowfoot grass, goosegrass, stinkgrass, velvetgrass, Hares Tall grass, canarygrass, smutgrass, wild garlic, nutsedge, clover, Johnsongrass, and walnut shells.

One or more of the aforementioned plant tissue may be used, as desired, such as two or more, such as three or more, such as four or more, such as five or more and including ten or more. Where cellulose nutrient components of interest include two or more different plant tissues, each type of plant tissue may be from 1% or more by weight of the total cellulose nutrient component, such as 5% or more by weight, such as 10% or more by weight, such as 15% or more by weight, such as 20% or more by weight and including 25% or more by weight. For example, where the cellulose nutrient component includes two or more different plant tissues, each plant tissue may range from 1% by weight to 99% by weight, such as from 5% by weight to 95% by weight, such as from 10% by weight to 90% by weight, such as from 15% by weight to 85% by weight, such as from 20% by weight to 80% by weight and including from 25% by weight to 75% by weight.

In embodiments, the ratio of carbon to nitrogen in the cellulose nutrient component varies depending on type of plant species employed in the cellulose nutrient composition. For example, the ratio of carbon to nitrogen in the cellulose nutrient may range from 10:1 to 90:1, such as from 15:1 to 85:1, such as from 20:1 to 80:1, such as from 25:1 to 75:1, such as from 30:1 to 70:1, such as from 35:1 to 65:1 and including from 40:1 to 60:1.

The cellulose nutrient component may be dry or green, as desired. By "dry" is meant that the plant tissue in the cellulose nutrient component is processed (e.g., under heat or ambient conditions) to remove water. Accordingly, in these embodiments the plant tissue in the cellulose nutrient component will include 1% w/w water or less, such as 0.5% w/w water or less, such as 0.25% w/w water or less, such as 0.1% w/w water or less, such as 0.05% w/w water or less, such as 0.01% w/w water or less and including 0.001% w/w water or less. By "green" is meant that the plant tissue is used in its natural state where water naturally present in the plant tissue is not removed prior to employing in the subject compositions.

The amount of the cellulose nutrient component in the subject compositions may vary. In some embodiments, the weight percent to cellulose nutrient component is 25% w/w or more, such as 30% w/w or more, such as 40% w/w or more, such as 50% w/w or more, such as 60% w/w or more, such as 70% w/w or more, such as 80% w/w or more, such as 90% w/w or more and including 95% w/w or more. For example, the weight percent of cellulose nutrient component may range from 25% w/w to 95% w/w, such as from 30% w/w to 90% w/w, such as from 35% w/w to 85% w/w, such as from 40% w/w to 80% w/w and including from 50% w/w to 70% w/w.

Microbial Blend Component

Compositions of interest also include a microbial blend component. The term "microbial" is used herein in its conventional sense to refer to microorganisms that can grow and proliferate in soil and may include but are not limited to bacteria and fungal species. In embodiments of the present invention, microbial blend species are capable of digesting and proliferating on the cellulose nutrient component and may be one or more of: antagonistic against a plurality of soil-borne pathogens, non-pathogenic towards plants and animals, readily grow and proliferate in soil and are suitably tolerant in elevated temperatures.

In embodiments, the microbial blend component may include one or more microbial species, such as one or more bacterial species, one or more fungal species or a combination thereof. For example, the microbial blend component may include two or more microbial species, such as three or more microbial species, such as five or more microbial species and including ten or more microbial species.

In some embodiments, the microbial blend component may include five or more distinct bacterial species. Bacterial species of interest may include, but are not limited to, bacterial species such as *Bacillus subtilis; Bacillus thuringiensis; Bacillus cereus; Bacillus megaterium; Bacillus penetrans; Arthrobacter paraffineus*; and *Pseudomonas fluorescens*. For example, the microbial blend component may include rhizobacteria.

In other embodiments, the microbial blend component may have two or more distinct fungal species, including but not limited to fungal species such as *Trichoderma viride, Trichoderma harzianum, Trichoderma polysporum, Trichoderma hamatum, Trichoderma koningii, Gliocladium virens,*

*Gieocladium roseum, Gliocladium catenulatum, Penicillium oxalicum, Penicillium lilacinum, Penicillium nigricans, Penicillium chrysogenum* and *Penicillium frequentens.*

Suitable microbial blends may also include, but are not limited to, those described in U.S. Pat. No. 6,871,446 filed Oct. 23, 2000, the disclosure of which is herein incorporated by reference in its entirety. In certain instances, the microbial blend may be a composition that is or is substantially the same as, a microbial inoculant commercially available under the trademark IOTA to Fusion 360 of Turlock, Calif.

In some embodiments, the microbial blend component includes one or more soil-borne pathogen antagonists. By "soil-borne pathogen antagonist" is meant the group of microorganisms which are active against pathogens that grow and proliferate in soil and may include microorganisms which are capable of inhibiting growth or reproduction of the soil-borne pathogens or otherwise preventing proliferation of the pathogen. In some embodiments, the microbial blend component includes microorganism species which are antagonistic to one or more of *Verticillium dahlia, Monilochaetes infuscans, Fusarium solani, Rhizoctonia solani, Cylindrocarpon obtusisporum, Sclerotinia scierotiorum, Pythium aphanidermatum, Sclerotinia minor, Phytophthora megasperma, Sclerotium rofsii, Phymatotrichum omnivorum* and *Botrytis cinerea,* among other soil-borne pathogen species. For example, microorganisms in the microbial blend component may be antagonistic to two or more of the aforementioned soil-borne pathogen species, such as three or more, such as four or more and including five or more of the aforementioned soil-borne pathogen species.

In some instances, the microbial blend component includes one or more plant parasitic nematode antagonists. The term "plant parasitic nematode antagonist" as used herein refers to microorganisms which are active against nematodes and may include growth inhibitors, reproductive inhibitors, nematotoxicants. As such, the microbial blend component according to certain embodiments may antagonize plant parasitic nematodes by inhibiting reproduction of new plant parasitic nematodes, killing plant parasitic nematodes, inhibiting or retarding the growth of existing plant parasitic nematodes or combinations thereof.

In certain embodiments, the microbial blend component includes a carrier medium, such as a solid or liquid carrier medium. Liquid carrier mediums of interest include aqueous mediums with or without additional components such as glycerin, alcohol, polymers, organic acids, microbial by-products such as amino acids, complex carbohydrates, macronutrients, micronutrients, vitamins & cofactors, sterols, proteins, gums (e.g. guar gum, xanthan gum), liquid fertilizers, liquid substrates. Solid carrier mediums of interest include, but are not limited to, solid media, e.g., inactivated seed, viable seed, prilled fertilizer, pelleted fertilizer, potting soil, compost, soybean or related meal, greenwaste and related organic waste, manure, fruit culls, talcum, dry mineral preparations, etc. and the like.

The amount of the microbial blend component in the subject compositions may vary. When present in a liquid medium, the total concentration of microbial species in the subject compositions may be about $1\times10^5$ cfu/ml or more, such as $1\times10^6$ cfu/ml or more, such as $1\times10^7$ cfu/ml or more, such as $1\times10^8$ cfu/ml or more, such as $1\times10^9$ cfu/ml or more and including $1\times10^{12}$ cfu/ml or more. For example, the total concentration of microbial species in the subject compositions may range from $1\times10^5$ cfu/ml to $1\times10^{15}$ cfu/ml, such as from $1\times10^6$ cfu/ml to $1\times10^{14}$ cfu/ml, such as from $1\times10^7$ cfu/ml to $1\times10^{13}$ cfu/ml, such as from $1\times10^8$ cfu/ml to $1\times10^{12}$ cfu/ml and including from $1\times10^9$ cfu/ml to $1\times10^{11}$ cfu/ml.

When combined in a solid medium, the total number of microbial species in the subject compositions may be $1\times10^3$ or more, such as $1\times10^4$ or more, such as $1\times10^5$ or more, such as $1\times10^6$ or more, such as $1\times10^7$ or more, such as $1\times10^8$ or more, such as $1\times10^9$ or more and including $1\times10^{12}$ or more. For example, the total number of microbial species in the subject compositions may range from $1\times10^2$ to $1\times10^{12}$, such as from $1\times10^3$ to $1\times10^{11}$, such as from $1\times10^4$ to $1\times10^{10}$, such as from $1\times10^5$ to $1\times10^9$ and including from $1\times10^6$ to $1\times10^8$.

In certain embodiments, the microbial blend component further includes an activator for activating proliferation of certain microbes. For example, the microbial blend component may include a mixture of complex carbohydrates, variable chain alcohols, catalysts, polycarboxylic acids, amino acids and proteins sufficient to activate rapid proliferation of certain microbes such as saprophytes, symbionts or competitors of plant pathogens (e.g., plant parasitic nematodes). In these embodiments, the amount of the activator in the microbial blend component ranges from about 1% to 35% w/w, such as 2% to 30% w/w, such as 5% to 25% w/w, such as 7% to 20% w/w and including 10% to 15% w/w. In certain instances, the activator may be a composition that is or is substantially the same as, a mixture commercially available under the trademark TILTH to Fusion 360 of Turlock, Calif.

Source of Nitrogen

Compositions of interest also include a source of nitrogen. Sources of nitrogen that find use in the subject compositions are nitrogen containing compounds which provide a readily assimilable source of nitrogen. In some embodiments, the nitrogen source is an inorganic source of nitrogen. In certain instances, the source of nitrogen is chemical nitrogen source. For example, chemical nitrogen sources my include, but are not limited to, nitrate nitrogen sources (e.g., calcium ammonium nitrates, ammonium nitrates, calcium nitrate, sodium nitrate, potassium nitrate, etc.) and ammonium nitrogen sources (e.g., anhydrous ammonia, urea, ammonium nitrate, nitrogen solutions such as urea-ammonium nitrate-water, ammonium sulfate, diammonium phosphate, monoammonium phosphate, ammonium polyphosphate, ammonium carbonate, etc.)

In embodiments of the invention, the amount of the nitrogen source component in the composition ranges from about 5% to 75% w/w, such as 10% to 60% w/w, such as 15% to 50% w/w, such as 20% to 40% w/w and including 25% to 35% w/w.

The source of nitrogen may be a single nitrogen containing compound or a combination of two or more different nitrogen containing compounds. For example, in some embodiments compositions include two or more nitrogen containing compounds, such as where the subject compositions include three or more nitrogen containing compounds, such as 4 or more nitrogen containing compounds and including 5 or more nitrogen containing compounds. Where the source of nitrogen includes two more nitrogen containing compounds, the percent by weight of each nitrogen containing compound in compositions of interest may vary, ranging from 5% to 75% w/w, such as 10% to 60% w/w, such as 15% to 50% w/w, such as 20% to 40% w/w and including 25% to 35% w/w. In certain embodiments, the source of nitrogen is a single nitrogen containing compound.

Source of Phosphorus

Compositions of interest also include a source of phosphorus. Sources of phosphorus that find use in the subject compositions are phosphorus containing compounds which provide a readily assimilable source of phosphorus. In some embodiments, the phosphorus source is a mineral source of phosphorus. For example, mineral phosphorus sources my include, but are not limited to, slag phosphate ($P_2O_5$), superphosphate, concentrated superphosphate, triple superphosphate, dicalcium phosphate, monoammonium phosphate, diammonium phosphate, ammonium polyphosphate as well as rock phosphate, such as mineral apatites ($Ca_5(PO_4)_3OH$, F,Cl), francolite ($Ca_{10-x-y}Na_x(PO_4)_{6-z})(CO_3)_2F_{0.4}F_2$), fluoroapatite ($Ca_5(PO_4)_3F$), hydroxyl-apatite ($Ca_5(PO_4)_3OH$), among other sources of mineral phosphorus.

In embodiments of the invention, the amount of the phosphorus source component in the composition ranges from about 5% to 75% w/w, such as 10% to 60% w/w, such as 15% to 50% w/w, such as 20% to 40% w/w and including 25% to 35% w/w.

The source of nitrogen may be a single phosphorus containing compound or a combination of two or more different phosphorus containing compounds. For example, in some embodiments compositions include two or more phosphorus containing compounds, such as where the subject compositions include three or more phosphorus containing compounds, such as 4 or more phosphorus containing compounds and including 5 or more phosphorus containing compounds. Where the source of phosphorus includes two more phosphorus containing compounds, the percent by weight of each phosphorus containing compound in compositions of interest may vary, ranging from 5% to 75% w/w, such as 10% to 60% w/w, such as 15% to 50% w/w, such as 20% to 40% w/w and including 25% to 35% w/w. In certain embodiments, the source of phosphorus is a single phosphorus containing compound.

Exotic Micronutrient Component

Exotic micronutrients of the subject compositions include a set or collection of non-traditional micronutrients, where the non-traditional micronutrients may be ones that provide ionic elements found in low amounts, e.g., low parts per million to parts per billion range, in virgin soils (i.e., soils that have not been used previously for agriculture). For example, non-traditional micronutrients may be micronutrients that promote the electrostatic bonding of amino acid chains. As such, powder or fine forms of oxidized coal, oxidized bituminous material, ironite, volcanic rock, shale, fossilized peat, moss, kelp or seaweed find use in the subject compositions to provide a source of one or more exotic micronutrients.

In some embodiments, compositions of interest may include 5 or more distinct exotic micronutrient ionic elements, such as 10 or more distinct exotic micronutrient ionic elements, such as 20 or more distinct exotic micronutrient ionic elements, such as 30 or more distinct exotic micronutrient ionic elements, such as 40 or more distinct exotic micronutrient ionic elements and including 50 or more distinct exotic micronutrient ionic elements.

Exotic micronutrient ionic elements of interest include, but are not limited to: Aluminum (Al), Antimony (Sb), Barium (Ba), Beryllium (Be), Bismuth (Bi), Boron (B), Bromine (Br), Cadmium (Cd), Cerium (Ce), Cesium (Cs), Chromium (Cr), Cobalt (Co), Dysprosium (Dy), Erbium (Er), Europium (Eu), Fluorine (F), Gadolinium (Gd), Gallium (Ga), Germanium (Ge), Gold (Au), Hafnium (Hf), Holmium (Ho), Indium (In), Lanthanum (La), Lutetium (Lu), Lithium (Li), Mercury (Hg), Molybdenum (Mo), Neodymium (Nd), Nickel (Ni), Niobium (Nb), Platinum (Pt), Praseodymium (Pr), Rhodium (Rh), Ruthenium (Ru), Samarium (Sm), Scandium (Sc), Selenium (Se), Silica (Si), Silver (Ag), Strontium (Sr), Sulfur (S), Tellurium (Te), Terbium (Tb), Thallium (Tl), Thorium (Th), Thulium (Tm), Tin (Sn), Titanium (Ti), Tungsten (W), Vanadium (V), Ytterbium (Yb), Yttrium (Y), and Zirconium (Zr).

Exotic micronutrients may be present in the form of salts which provide for the desired ionic elements. Examples of sources salts are summarized in Table 1. The below list of sources of the exotic are merely representative.

TABLE 1

| Exotic Micronutrient Element | Symbol | Source: Nitrates | Source: Chlorides | Source: Sulfides | Source: Oxides | Source: Misc. |
|---|---|---|---|---|---|---|
| Europium | Eu | $Eu(NO_3)_3$ | $EuCl_3$ | $Eu_2(SO_4)_3$ | $Eu(OH)_3$ $Eu_2O_3$ | |
| Fluorine | F | $FNO_3$ | | | $F_2O$ | $C_2H_4FNO$: Fluoroacetamide $C_2H_3FO_2$: Fluoroacetic Acid $ClFO_4$: Perchlorate |
| Gadolinium | Gd | $Gd(NO_3)_3$ | $GdCl_3$ | $Gd_2(SO_4)_3$ | $Gd(OH)_3$ $Gd_2O_3$ | |
| Gallium | Ga | $Ga(NO_3)_3$ | $GaCl_3$ | $Ga_2(SO_4)_3$ | $Ga(OH)_3$ $Ga_2O_3$ | |
| Germanium | Ge | | $Cl_2Ge$ $Cl_4Ge$ | | $GeO_2$ | $F_4Ge$: Tetrafluoride |
| Gold | Au | | $AuCl$ | $Au_2S$ | $Au_2O$ | CAuN: Monocyanide AuI: Monoiodide |
| Hafnium | Hf | | $HfCl_4$ | $Hf(SO_4)$ | $HfO_2$ | |
| Holmium | Ho | | $HoCl_3$ | | $Ho_2O_3$ | $HoB_3$: Bromide $HoI_3$: Iodide |
| Indium | In | | $Cl_3In$ | $In_2O_{12}S_3$ | $In_2O_3$ | InP: Phosphide AsIn: Arsenide |
| Lanthanum | La | $La(NO_3)_3$ | $LaCl_3$ | $La_2(SO_4)_3$ | $La(OH)_3$ $La_2O_3$ | |
| Lithium | Li | $LiNO_3$ | $ClLi$ | $Li_2O_4S$ | $HLiO$ $Li_2O$ | |
| Lutetium | Lu | | $LuCl_3$ | $Lu_2(SO_4)_3$ | $Lu_2O_3$ | |
| Neodymium | Nd | $Nd(NO_3)_3$ | $NdCl_3$ | $Nd_2(SO_4)_3$ | $Nd(OH)_3$ $Nd_2O_3$ | |
| Nickel | Ni | $N_2NiO_6$ | $Cl_2Ni$ | $NiO_4S$ | $H_2NiO_2$ $Ni_2O_3$ | |

TABLE 1-continued

| Exotic Micronutrient Element | Symbol | Source: Nitrates | Source: Chlorides | Source: Sulfides | Source: Oxides | Source: Misc. |
|---|---|---|---|---|---|---|
| Niobium | Nb | | $Cl_5Nb$ | | $Nb_2O_5$ | $F_4Nb$ Pentafluoride<br>$F_7K_2NbO$ Oxypenafluoride |
| Platinum | Pt | na | na | na | na | |
| Praseodymium | Pr | | $PrCl_3$ | $Pr_2(SO_4)_3$ | $Pr(OH)_3$<br>$PrO_2$<br>$Pr_2O_3$ | |
| Rhodium | Rh | | $C_4Cl_2O_4Rh_2$<br>$Cl_3Rh$ | | | |
| Ruthenium | Ru | | $Cl_3Ru$<br>$Cl_6H_{42}N_{14}$<br>$O_2Ru$ | | $O_4Ru$ | |
| Samarium | Sm | | $SmCl_2$<br>$SmCl_3$ | $Sm_2(SO_4)_3$ | $Sm(OH)_3$<br>$Sm_2O_3$ | |
| Scandium | Sc | $Sc(NO_3)_3$ | $ScCl_3$ | $Sc_2(SO_4)_3$ | $Sc(OH)_3$<br>$O_3Sc_2$ | |
| Silicon | Si | | $Cl_4Si$ | $S_2Si$: Disulfide | $OSi$<br>$O_2Si$ | $F_4Si$: Tetrafluoride<br>CSi: Carbide<br>$Br_4Si$: Tetrabromide |
| Silver | Ag | $AgNO_2$<br>$Ag(NO_3)_3$ | $AgCl$<br>$AgClO_4$ | $Ag_2S$<br>$Ag_2O_4S$ | $AgO$<br>$Ag_2O$<br>$C_2Ag_2O_4$ | AgI: Iodide<br>AgF: Fluoride |
| Strontium | Sr | $N_2O_6Sr$ | $Cl_2Sr$<br>$Cl_2O_6Sr$ | $O_4SSr$ | $OSr$<br>$O_2Sr$<br>$H_2O_2Sr$ | $F_2Sr$: Floride |
| Sulfur | S | | $Cl_2S_2$<br>$Cl_2O_2S$ | | $O_2S$<br>$O_3S$ | $H_2O_4S$: Sulfuric Acid<br>SI: Iodide<br>$F_4S$: Tetrafluoride |
| Tellurium | Te | | $Cl_2Te$<br>$Cl_4Te$ | | $O_2Te$ | $Br_2Te$: Tetrabromide<br>$F_6Te$: Tetrafluoride<br>$H_2O_3Te$: Telluric Acid |
| Terbium | Tb | $Tb(NO_3)_3$ | $TbCl_3 6H_2O$ | | $O_3Tb_2$<br>$Tb_4O_7$ | |
| Thallium | Tl | $NO_3Tl$ | $Cl_3Tl$ | $STl_2$<br>$O_4STl_2$ | $HOTl$<br>$OTl_2$ | $C_2H_3O_2Tl$: Acetate |
| Thorium | Th | $N_4O_{12}Th$ | $Cl_4Th$ | $O_8S_2Th$ | $O_2Th$ | $I_4Th$: Iodide |
| Thulium | Tm | $Tm(NO_3)_3$ | $TmCl_3 7H_2O$ | $Tm_2(SO_4)_3 8_2HO$ | $Tm(OH)_3$<br>$O_3Tm_2$ | $TM_2(C_2O_4)_3 6H_2O$: OOxalate hexahydrate |
| Tin | Sn | | | | $SnO$ | $Sn_4P_3$: Phosphides |
| Titanium | Ti | | $C_{10}H_{10}Cl_2Ti$<br>$Cl_2Ti$<br>$Cl_3Ti$<br>$Cl_4Ti$ | $O_5STi$<br>$O_{12}S_3Ti_2$ | $O_2Ti$ | $F_4Ti$: Tetrafluoride<br>$H_2Ti$: Hydride |
| Tungsten | W | | | | $O_3W$ | $F_6W$: Hexafluoride<br>$H_2O_4W$: Tungstic Acid |
| Vanadium | V | | $Cl_2OV$<br>$Cl_3OV$ | $O_5SV$<br>$S_3V_2$<br>$O_{12}S_3V_2$ | $O_3V_2$<br>$O_5V_2$ | $F_3V$: Trifluoride<br>$F_4V$: Tetrafluoride<br>$F_5V$: Pentafluoride |
| Ytterbium | Yb | $Yb(NO_3)_3$ | $YbCl_3$ | $Yb_2(SO_4)_3$ | $O_3Yb_2$ | |
| Yttrium | Y | $Y(NO_3)_3$ | $YCl_3$ | $Y_2(SO_4)_3$ | $O_3Y_2Y(OH)_3$ | |
| Zirconium | Zr | $N_4O_{12}Zr$ | $Cl_4Zr$<br>$Cl_2OZr$ | $O_8S_2Zr$ | $O_2Zr$<br>$H_4O_4Zr$ | $ZrF_4$: Tetrafluoride<br>$ZrH_2$: Hydride<br>$I_4Zr$: Iodide |

The overall amount of exotic micronutrient present may vary where in certain embodiments, the amount ranges from 0.001 ppb to 100 ppb w/w, such as 0.005 ppb to 75 ppb w/w, such as 0.01 ppb to 50 ppb w/w, such as 0.05 ppb to 25 ppb w/w and including 0.01 ppb to 10 ppb w/w.

The amounts of individual exotic micronutrients may be chosen to provide for concentrations of elements as desired, where the desired concentrations of elements may vary, depending on the particular nature of the exotic micronutrient. For example, one class of exotic micronutrients may be viewed as "severe" micronutrients, and includes Hg (Mercury), Cd (Cadmium), Cs (Cesium). The amounts of these micronutrients may be chosen to provide a concentration in the concentrated product ranging from 1 to 10 ppb, such as 7.5 ppb. Another class of exotic micronutrients may be viewed as "intermediate" micronutrients, and includes Se (Selenium), Al (Aluminum), Ba (Barium), Be (Beryllium), B (Boron), Cr (Chromium), Dy (Dysprosium), Ga (Gallium), La (Lanthanum), Ni (Nickel), Ru (Ruthenium), Sr (Strontium), Te (Tellurium), Sn (Tin), V (Vanadium). The amounts of these micronutrients may be chosen to provide a concentration in the concentrated product ranging from 10 to 25 ppb, such as 15 ppb. Another class of exotic micronutrients may be viewed as "Standard I" micronutrients, and includes Mo (Molybdenum), Sb (Antimony), Ce (Cerium), Co (Cobalt), Er (Erbium), Gd (Gadolinium), Ge (Germanium), Hf (Hafnium), Lu (Lutetium), Li (Lithium), Rh (Rhodium), Sm (Samarium), Ti (Titanium), W (Tungsten), Yb (Ytterbium), Zr (Zirconium). The amounts of these micronutrients may be chosen to provide a concentration in the concentrated product ranging from 20 to 40 ppb, such as 35 ppb. Another class of exotic micronutrients may be viewed as "Standard II" micronutrients, and includes Bi (Bismuth), Eu (Europium), Ho (Holmium), Nd (Neodymium), Pt (Platinum), Ag (Silver), Tl (Thallium), Th (Thorium). The amounts of these micronutrients may be chosen to provide a concentration in the concentrated product ranging from 95 to 150 ppb, such as 90 ppb. Another class of exotic micronutrients may be viewed as "Standard III" micronutrients, and includes Br (Bromine), F (Fluorine), Au (Gold), In (Indium), Pr (Praseodymium), Tb (Terbium), Tm (Thulium). The amounts of these micronutrients may be chosen to provide a concentration in the concentrated product ranging from 400 to 1,000 ppb, such as 850 ppb. Another class of exotic micronutrients may be viewed as "Standard IV" micronutrients, and includes Nb (Niobium), Sc (Scandium), Si (Silicon), S (Sulfur), Y (Yttrium). The amounts of these micronutrients may be chosen to provide a concentration in the concentrated product ranging from 2,000 to 3,700 ppb, such as 3,200 ppb.

An embodiment of the an exotic micronutrient component of interest is one that provides ionic species of the following elements in the amounts provided below: (1) Hg (Mercury), Cd (Cadmium), and Cs (Cesium) ranging from 1 to 10 ppb, such as 7.5 ppb; (2) Se (Selenium), Al (Aluminum), Ba (Barium), Be (Beryllium), B (Boron), Cr (Chromium), Dy (Dysprosium), Ga (Gallium), La (Lanthanum), Ni (Nickel), Ru (Ruthenium), Sr (Strontium), Te (Tellurium), Sn (Tin), V (Vanadium) ranging from 10 to 25 ppb, such as 15 ppb; (3) Mo (Molybdenum), Sb (Antimony), Ce (Cerium), Co (Cobalt), Er (Erbium), Gd (Gadolinium), Ge (Germanium), Hf (Hafnium), Lu (Lutetium), Li (Lithium), Rh (Rhodium), Sm (Samarium), Ti (Titanium), W (Tungsten), Yb (Ytterbium), Zr (Zirconium) ranging from 20 to 40 ppb, such as 35 ppb; (4) Bi (Bismuth), Eu (Europium), Ho (Holmium), Nd (Neodymium), Pt (Platinum), Ag (Silver), Tl (Thallium), Th (Thorium) ranging from 95 to 150 ppb, such as 90 ppb; (5) Br (Bromine), F (Fluorine), Au (Gold), In (Indium), Pr (Praseodymium), Tb (Terbium), Tm (Thulium) ranging from 400 to 1,000 ppb, such as 850 ppb; and (6) Nb (Niobium), Sc (Scandium), Si (Silicon), S (Sulfur), Y (Yttrium) ranging from 2,000 to 3,700 ppb, such as 3,200 ppb.

Alternatively, at least some if not all of the micronutrients may be obtained from a naturally occurring source of nutrients, e.g., fulvic acid. In certain embodiments, fulvic acid is itself the exotic micronutrient source. In such embodiments, fulvic acid is used in greater amounts than when it is employed as a complexing agent (e.g., as described in U.S. Pat. No. 6,874,277, herein incorporated by reference), where this greater amount may be 3-fold or more greater, such as 5-fold or more greater. Additional sources of the exotic micronutrient component include, but are not limited to: quarry from Gold (Au) and Copper (Cu) mines; Leonardite; Volcanic Hot Spring Water (Gilroy Hot Springs, Prizmatic Hot Springs—Yellowstone); Ironite Granule (Scottsdale, Ariz.); and the like.

Additional Components

In some embodiments, compositions may also include one or more of a carbon skeleton energy component, macronutrients, micronutrients, vitamin cofactors, a complexing agent, an ionophore, each of which is described in greater detail below.

Carbon Skeleton Energy Compounds

CSE compounds that find use in the subject compositions are carbon containing substances which provide a readily assimilable source of both carbon and energy. In certain embodiments, the CSE component provides a complex array of various carbon compounds. The carbon skeleton energy component is a $C_2$ to $C_{10}$ containing compound or polymer thereof, e.g., a polymer in which the monomeric units are $C_2$ to $C_{10}$ compounds, such as a polysaccharide, including a $C_4$ to $C_8$ containing compound or polymer.

CSE compounds of interest include: complex organic compositions, such as molasses (e.g. cane, sugar beet, sorghum, etc.), whey, corn steep liquor, grape syrup, maple syrup, corn syrup, etc; sugars, e.g. sucrose, fructose, glucose, lactose, galactose, dextrose, maltose, raffinose, ribose, ribulose, xylulose, xylose, amylose, arabinose, etc.; sugar phosphates, e.g. fucose-P, galactose-P, glucose-P, lactose-P, maltose-P, mannose-P, ribose-P, ribulose-P, xylose-P, xylulose-P, etc.; sugar alcohols, e.g. adonitol, sorbitol, mannitol, maltitol, ribitol, galactitol, glucitol, etc.; organic acids, e.g. gluccuronic acid, alpha ketoglutaric acid, galactonic acid, glucaric acid, gluconic acid, pyruvic acid, polygalacturonic acid, citric acid, succinic acid, malic acid, isocitric acid, folic acid, etc.; nucleotides and bases, e.g. adenosine, adenosine-P, uridine, uridine-P, thymine, thymine-P, cytosine, cytosine-P, guanine, guanine-P, etc.; and amino acids, e.g. glycine, alanine, leucine, isoleucine, asparagine, tyrosine, phenylalanine, serine, cysteine, valine, proline, methionine, glutamine, threonine, lysine, aspartic acid, glutamic acid, arginine, and the like.

In embodiments of the invention, the amount of CSE component in the composition ranges from about 5% to 75% w/w, such as 10% to 60% w/w, such as 15% to 50% w/w, such as 20% to 40% w/w and including 25% to 35% w/w.

The CSE component may be a single carbon containing compound or a combination of two or more different carbon containing compounds. For example, in some embodiments compositions include two or more carbon containing compounds or polymers, such as where the subject compositions include three or more carbon containing compounds or polymers, such as 4 or more carbon containing compounds or polymers and including 5 or more carbon containing compounds or polymers. Where the CSE component includes two more carbon containing compounds or polymers, the percent by weight of each carbon containing compound in compositions of interest may vary, ranging from 5% to 75% w/w, such as 10% to 60% w/w, such as 15% to 50% w/w, such as 20% to 40% w/w and including 25% to 35% w/w. In certain embodiments, the CSE component is a single carbon containing compound or polymer. In some instances, the carbon skeleton energy compound is corn syrup. In other instances, the carbon skeleton energy compound is cane molasses.

Macronutrients

As noted above, the compositions include one or more macronutrients. As the macronutrient component is a compound that is used by the subject plants, it is typically water soluble so as to be in a form that may be easily used by a plant. The subject compositions may include one or a plurality of macronutrient components. Accordingly, the number of macronutrient components present in a composition may range from 1 to 15 or more, e.g., from 1 to 6, e.g., from 2 to 6.

The total amount of macronutrient component present in a given composition (whether one or a plurality of macronutrients) depends on a variety of factors such as the particular plant to which the composition is to be administered, the particular macronutrient component(s) employed, and the like. In many embodiments, the total amount of macronutrient component in the composition may range from about 0.01% to about 25% w/w, e.g., from about 1% to about 20% w/w, e.g., from about 1 to about 15% w/w. Exemplary macronutrient components include, but are not limited to one or more of: N, P, K, Ca, Mg, S, Cl, Na, C, H, O. For example, certain embodiments may include one or more of the following exemplary macronutrient components:

R—ammonium nitrate, monoammonium phosphate, ammonium phosphate sulfate, ammonium sulfates, ammonium phosphatenitrate, diammonium phosphate, ammoniated single superphosphate, ammoniated triple superphosphate, nitric phosphates, ammonium chloride, aqua ammonia, ammonia-ammonium nitrate solutions, calcium ammonium nitrate, calcium nitrate, calcium cyanamide, sodium nitrate, urea, urea-formaldehyde, urea-ammonium nitrate solution, nitrate of soda potash, potassium nitrate, amino acids, proteins, nucleic acids P—superphosphate (single, double and/or triple), phosphoric acid, ammonium phosphate, ammonium phosphate sulfate, ammonium phosphate nitrate, diammonium phosphate, ammoniated single superphosphate, ammoniated single superphosphate, ammoniated triple superphosphate, nitric phosphates, potassium pyrophosphates, sodium pyrophosphate, nucleic acid phosphates K—potassium chloride, potassium sulfate, potassium gluconate, sulfate of potash magnesia, potassium carbonate, potassium acetate, potassium citrate, potassium hydroxide, potassium manganate, potassium phosphate, potassium molybdate, potassium thiosulfate, potassium zinc sulfate Ca—calcium ammonium nitrate, calcium nitrate, calcium cyanamide, calcium acetate, calcium acetylsalicylate, calcium borate, calcium borogluconate, calcium carbonate, calcium chloride, calcium citrate, calcium ferrous citrate, calcium gluconate, calcium glycerophosphate, calcium lactate, calcium oxide, calcium pantothenate, calcium proprionate, calcium saccharate, calcium sulfate, calcium tartrate Mg—magnesium oxide, dolomite, magnesium acetate, magnesium benzoate, magnesium bisulfate, magnesium borate, magnesium chloride, magnesium citrate, magnesium gluconate, magnesium nitrate, magnesium phosphate, magnesium salicylate, magnesium sulfate S—ammonium sulfate, ammonium phosphate sulfate, calcium sulfate, potassium sulfate, magnesium sulfate, sulfuric acid, cobalt sulfate, copper sulfate, ferric sulfate, ferrous sulfate, sulfur, cysteine, methionine Where the macronutrient component includes two or more compounds, the percent by weight of each macronutrient compound in compositions of interest may vary, ranging from about 0.01% to about 25% w/w, e.g., from about 1% to about 20% w/w, e.g., from about 1 to about 15% w/w. In certain embodiments, the macronutrient component includes a single macronutrient. In certain instances, the macronutrient is calcium gluconate.

Micronutrients

In certain embodiments, the subject compositions may also include one or more micronutrient components. As the micronutrient components are components that are used by a plant, they are typically water soluble components so as to be in a form that may be easily used by a plant. The subject compositions may include one or a plurality of micronutrient components. Accordingly, the number of micronutrient components present in a composition may range from about 1 to about 60 or more, e.g., from about 3 to about 55, e.g., from about 4 to about 50.

The total amount of micronutrient component present in a given composition, whether a single or a plurality of micronutrients depends on the type of subject plants and may range from about 0.001 ppm to 500 ppm w/w, such as 0.05 to 400 ppm w/w, such as 0.01 ppm to 300 ppm, such as 0.1 ppm to 250 ppm and including 1 ppm to 200 ppm w/w. Micronutrient compounds of interest include, but are not limited to:

Zn—zinc oxide, zinc acetate, zinc benzoate, zinc chloride, zinc citrate, zinc nitrate, zinc salicylate, ziram.

Fe—ferric chloride, ferric citrate, ferric fructose, ferric glycerophosphate, ferric nitrate, ferric oxide (saccharated), ferrous chloride, ferrous citrate ferrous fumarate, ferrous gluconate, ferrous succinate.

Mn—manganese acetate, manganese chloride, manganese nitrate, manganese phosphate.

Cu—cupric acetate, cupric butyrate, cupric chlorate, cupric chloride, cupric citrate, cupric gluconate, cupric glycinate, cupric nitrate, cupric salicylate, cuprous acetate, cuprous chloride.

B—calcium borate, potassium borohydride, borax, boron trioxide, potassium borotartrate, potassium tetraborate, sodium borate, sodium borohydride, sodium tetraborate.

Mo—molybdic acid, calcium molybdate, potassium molybdate, sodium molybdate.

Co—cobaltic acetate, cobaltous acetate, cobaltous chloride, cobaltous oxalate, cobaltous potassium sulfate, cobaltous sulfate.

Where the micronutrient component includes two or more compounds, the percent by weight of each micronutrient compound in compositions of interest may vary, ranging from about 0.001 ppm to 500 ppm w/w, such as 0.05 to 400 ppm w/w, such as 0.01 ppm to 300 ppm, such as 0.1 ppm to 250 ppm and including 1 ppm to 200 ppm w/w.

Vitamins and Cofactor Composition

Compositions of interest also include one or more vitamin and cofactor compositions. The subject composition may include one or a plurality of vitamin and cofactor components. Accordingly, the number of vitamin and cofactor components present in a composition may range from about 1 to about 20 or more, e.g., from about 3 to about 15, e.g., from about 5 to about 12.

The total amount of vitamin and cofactor component present in a given composition, whether one or a plurality of vitamin/cofactor components depends on a variety of factors such as the subject plants, the particular vitamin cofactor component(s) employed, and the like. In many embodiments, the total amount of vitamin/cofactor component in the composition may range from about 0.001 to 10%, such as 0.01 to 5%, including 0.25 to 3.0% w/w. Vitamin and cofactors of interest include, but are not limited to:

Thiamine—thiamine pyrophosphate, thiamine monophosphate, thiamine disulfide, thiamine mononitrate, thiamine phosphoric acid ester chloride, thiamine phosphoric acid ester phosphate salt, thiamine 1,5 salt, thiamine triphosphoric acid ester, thiamine triphosphoric acid salt, yeast, yeast extract.

Riboflavin—riboflavin acetyl phosphate, flavin adenine dinucleotide, flavin adenine mononucleotide, riboflavin phosphate, yeast, yeast extract.

Nicotinic acid—nicotinic acid adenine dinucleotide, nicotinic acid amide, nicotinic acid benzyl ester, nicotinic acid monoethanolamine salt, yeast, yeast extract, nicotinic acid hydrazide, nicotinic acid hydroxamate, nicotinic acid-N-(hydroxymethyl)amide, nicotinic acid methyl ester, nicotinic acid mononucleotide, nicotinic acid nitrile.

Pyridoxine—pyridoxal phosphate, yeast, yeast extract.

Folic acid—yeast, yeast extract, folinic acid.

Biotin—biotin sulfoxide, yeast, yeast extract, biotin 4-amidobenzoic acid, biotin amidocaproate N-hydroxysuccinimide ester, biotin 6-amidoquinoline, biotin hydrazide, biotin methyl ester, d-biotin-N-hydroxysuccinimide ester, biotin-maleimide, d-biotin p-nitrophenyl ester, biotin propranolal, 5-(N-biotinyl)-3 aminoallyl)-uridine 5'-triphosphate, biotinylated uridine 5'-triphosphate, N-e-biotinyl-lysine.

Pantothenic acid—yeast, yeast extract, coenzyme A.

Cyanocobalamin—yeast, yeast extract.

Phosphatidylcholine—soybean oil, eggs, bovine heart, bovine brain, bovine liver, L-a-phosphatidylcholine, B-acetyl-g-O-alkyl, D-a-phosphatidylcholine (PTCn), B-acetyl-g-O-hexadecyl, DL-a-PTCh, B-acetyl-g-O-hexadecyl, L-a-PTCh, B-acetyl-g-O-(octadec-9-cis-e-nyl), L-a-PTCh, B-arachidonoyl, g-stearoyl, L-a-PTCh, diarachidoyl, L-a-PTCh, dibehenoyl(dibutyroyl, dicaproyl, dicapryloyl, didecanoyl, dielaidoyl, 12 diheptadecanoyl, diheptanoyl), DL-a-PTCh dilauroyl, La-PTCh dimyristoyl(dilauroyl, dilinoleoyl, dinonanoyl, dioleoyl, dipentadeconoyl, dipalmitoyl, distearoyl, diundecanoyl, divaleroyl, B-elaidoyl-a-palmitoyl, B-linoleoyl-a-palmitoyl)DL-a-PTCh di-O-hexadecyl(dioleoyl, dipalmitoyl, B—O-methyl-g-O-hexadecyl, B-oleoyl-g-O-hexadecyl, B-palmitoyl-g-O-hexadecyl), D-a-PTCh dipalmitoyl, L-a-PTCh, B—O-methyl-g-O-octadecyl, L-a-PTCh, B—(NBD-aminohexanoyl)-g-palmitoyl, L-a-PTCh, B-oleoyl-g-O-palmitoyl(stearoyl), L-a-PTCh, B-palmitoyl-g-oleoyl, L-a-PTCh, B-palmitoyl-a-(pyren 1-yl)hexanoyl, L-a-PTCh, B (pyren-1-yl)-decanoyl-g-palmitoyl, L-a-PTCh, B-(pyren-1-yl)-hexanoyl-g-palmitoyl, L-a-PTCh, B-stearoyl-g-oleoyl.

Inositol—inositol monophosphate, inositol macinate, myo-inositol, epi-inositol, myo-inositol 2,2'anhydro-2-c-hydroxymethyl(2-c-methylene-my-oinositol oxide), D-myo-inositol 1,4-bisphosphate, DL-myo-inositol 1,2-cyclic monophosphate, myo-inositol dehydrogenase, myo-inositol hexanicotinate, inositol hexaphosphate, myo-inositol hexasulfate, myo-inositol 2-monophosphate, D-myo-inositol 1-monophosphate, DL-myo-inositol 1-monophosphate, D-Myo-inositol triphosphate, scyllo-inositol.

PABA—m-aminobenzoic acid, O-aminobenzoic acid, p-aminobenzoic acid butyl ester, PABA ethyl ester, 3-ABA ethyl ester.

Where the vitamin and cofactor compositions includes two or more compounds, the percent by weight of each vitamin or cofactor compound in compositions of interest may vary, ranging from about 0.001 to 10%, such as 0.01 to 5%, including 0.25 to 3.0% w/w.

Complexing Agents

In certain embodiments, the subject compositions may also include one or more complexing agents. A "complexing agent" is used to in its conventional sense to refer to an agent that aids in the solubilization of components of the composition and may also serve to tie up ions (e.g., iron or other ions) and preventing formation of precipitates upon application. A complexing agent may be an agent that is capable of complexing with a metal ion. As such, powder or fine forms of oxidized coal, oxidized bituminous material, ironite, volcanic rock, shale, fossilized peat, moss, kelp or seaweed find use in the subject compositions to provide a source of one or more complexing agents. Other complexing agents of interest include, but are not limited to: citric acid, lignosulfonates, e.g., Ca—, K—, Na—, and ammonium lignosulfonates, amino acids, propionic acid and nucleic acids. In some instances, the secondary complexing agent may be a chelating agent, such as ethylenediamin tetraacetatic acid (EDTA), diethylene triamine pentacetic acid (DTPA), nitrolotriacetic acid (NTA), ethylenediaminediacetate (EDDA), ethylenediaminedi (o-hydroxyphenylacetic) acid (EDDHA), hydroxyethylethylene-diaminetriacetic acid (HEDTA), cyclohexane diamine tetraacetic acid (CDTA) and the like. Naturally occurring chelating agents may also be employed. By naturally occurring chelating agent is meant that the chelating agent is a chelating agent that occurs in nature, i.e. not an agent that has been first synthesized by human intervention. The naturally occurring chelating agent may be a low molecular weight chelating agent, where by low molecular weight chelating agent is meant that the molecular weight of the chelating agent does not exceed about 200 daltons. In certain embodiments, the molecular weight of the chelating agent is greater than about 100 daltons.

Naturally occurring low molecular weight chelating agents that may be used are microbial produced chelating agents, where by "microbial produced" is meant that the chelating agent is produced by a microbe, where the microbe is generally a bacterium or a fungus. In many embodiments, the chelating agents are citric acid cycle intermediates and derivatives thereof. Specific chelating agents of interest include: malic acid, succinic acid, oxalacetic acid, ketoglutaric acid and citric acid and amino acids derived from citric acid cycle intermediates, such as glycine (75.1 daltons), alanine (89.1 daltons), serine (105.1 daltons), valine (117.2 daltons), threonine (119.1 daltons), cysteine (121.2 daltons), leucine (131.2 daltons), isoleucine (131.2 daltons), asparginine (132.1 daltons), glutamine (146.2 daltons), methionine (149.2 daltons), etc. Accordingly, embodiments include compositions that may include a source of at least one naturally occurring chelating agent. By source is meant that the compositions may include the chelating agents or an entity or component that produces the chelating agents. In many embodiments, the source of chelating agents is a living or viable microbial source of chelating agents. For example, the microbial source may be a bacterial or fungal culture which produces the requisite chelating agents.

The total amount of complexing agent present in a given composition (whether one or a plurality of complexing agents) depends on a variety of factors such as the particular plant to which the composition is to be administered, the particular complexing agent(s) employed, and the like. In certain embodiments, the total amount of complexing agent in the composition may range from about 0.01 to about 5% w/w, e.g., from about 0.1% to about 4.5% w/w, e.g., from about 1.0% to about 4% w/w.

Ionophore Component

Compositions of interest also include an ionophore. The term "ionophore" is used in its conventional sense to refer to the class of organic compounds that are capable of transporting ions across lipid barriers in a plant cell. Ionophores of interest include, but are not limited to antibiotics, such as Gramicidin A and Valinomycin, and Amino Butyric Acids (ABA), such as D-alpha ABA, DL-alpha ABA, L-alpha ABA, DL-Beta ABA, Gama—ABA (GABA) (e.g., 4-GABA), and the like.

The total amount of ionophore in the subject compositions may range from about 10 ppm to 500 ppm w/w, such as 25 ppm to 450 ppm w/w, such as 50 ppm to 400 ppm w/w, such as 75 ppm to 350 ppm w/w, such as 100 ppm to 300 ppm and including 150 ppm to 250 ppm w/w, for example 200 ppm w/w.

Binder

As described in greater detail below, compositions of interest may be pelletized. Where the subject compositions are pelletized, the pellet may include one or more binder components. By "binder" is meant one or more compounds used to hold the pelletized composition together in a cohesive mix. As such, the binder may be any suitable compound which is sufficient to allow the pelletized composition to retain its shape. For example, binders may be organic or inorganic and include, but are not limited to, alumina, aluminates, aluminum, aluminum phosphate, attapulgite, borate class, calcium chromites, calcium fluoride, calcium germinate, calcium oxide, calcium lignosulfate, calcium aluminate, calcium sulfate, clay, iron humate, iron oxide, lime, magnesium chloride, magnesium oxide, magnesium lignosulfate, magnesium sulfate, Portland cement, potassium silicate, potassium lignosulfate, silicon carbine, sodium silicate, sodium lignosulfate, wollastonite, zinc sulfate hydrate, alginic acid, araldite, asphalt, bitumens, carbohydrates, casein, butadiene chloroprene, epoxy resins, glycerol, glycol ester derivatives, gums (e.g. guar gum, xanthan gum), hydroxylamine derivatives, nitrophenols, lupines, manioc flour, molasses, organosilicones, phenol borates and phosphates, acrylamides, polyamides, polyester resins, polyurethanes, sawdust, shale bitumen, shellac, tartrates, corn starch, sifted wheat flour, sifted corn flour, sifted rice flour, commercial anti-caking agents, silica-based anti-caking agents, hygroscopic absorption agents.

In embodiments of the invention, the amount of binder in the pelletized composition ranges from about 1% to 25% w/w, such as 2% to 20% w/w, such as 3% to 15% w/w and including 5% to 10% w/w. In embodiments, the ratio of cellulose nutrient component to binder varies depending on type pellets (e.g., size and shape) desired. For example, the weight ratio of cellulose nutrient component to binder may range from 1:1 to 25:1, such as from 2:1 to 20:1, such as from 3:1 to 15:1, such as from 4:1 to 10:1, and including from 5:1 to 8:1. In certain embodiments, the weight ratio of cellulose nutrient component to binder is 5:1

Wood

Compositions of interest also include an amount of wood. Wood present in the subject composition may be any suitable type of wood desired, depending on the cellulose nutrient component and type of microbes present in the microbial blend component. For example, suitable types of wood may include, but is not limited to pine, cedar, celery-top pine, cypress, Douglas-fir, European yew, fir, hemlock, Huon pine, kauri, nutmeg-yew, larch, red cedar, redwood, cherry, rimu, sprice, sugi, white cedar, Nootka cypress, abachi, African padauk, afzelia, agba, alder, American chestnut, ash, aspen, ayan, balsa, basswood, beech, birch, blackbean, black tupelo, blackwood, boxelder, boxwood, Brazilian walnut, Brazilwood, bubinga, buckeye, butternut, bay laurel, camphor, carapa, catalpa, Ceylon satinwood, coachwood, cocobolo, corkwood, cottonwood, cucumbertree, dogwood, ebony, elm, eucalyptus, crabapple, pear, greenheart, granadilla, guanandi, gum, hackberry, hickory, hornbeam, hophornbeam, iroko, ironwood, kingwood, lacewood, limba, locust, mahagony, maple, marblewood, marri, meranti, merbau, oak, okoume, olive, pink ivory, poplar, purpleheart, ramin, redheart, sweetgum, sandalwood, sapele, sassafras, silky oak, silver wattle, sourwood, tamboti, teak, rosewood, tupelo, turpentine, walnut, wenge, willow, and zingana among others.

Wood may be incorporated into the subject compositions in any convenient form, such as shavings, wood resin, powder, dust, particles, pellets, etc. The total amount of wood in the subject compositions may range from about 5% to 75% w/w, such as 10% to 60% w/w, such as 15% to 50% w/w, such as 20% to 40% w/w and including 25% to 35% w/w.

Methods for Fertilizing and Remediating Soil

As summarized above, aspects of the invention also include methods for fertilizing and remediating soil by treating soil with the subject compositions. As described above, the term "fertilizing" is used herein in its conventional sense to refer to providing or supplementing essential nutrients to the soil. Fertilizing may be passive, such as where the subject compositions provide a source of essential nutrients to target plants. Alternatively, fertilizing may be active, such as where the subject composition initiates, catalyzes or otherwise facilitates uptake of the essential nutrients by plants in the soil. In certain embodiments, fertilizing the soil may be realized by an enhancement in the overall health of plants in soil contacted with the subject composition, where in some instances the desired enhancement ultimately results in greater production of some desirable parameter, such as for example the amount of harvestable crop produced.

For example, in some embodiments enhanced overall health of the subject plants by compositions of interest includes an increased amount of harvested crop, such as by 10% or more, such as by 25% or more, such as by 50% or more, such as by 75% or more and including increasing the amount of harvested crop by 100% or more, e.g., as compared to a suitable reference or control, such as described above. For example, the increased amount of harvested crop may range from 10% to 100%, such as from 25% to 75% and including from 30% to 60%. In other instances, compositions of interest may increase harvested crop production by 1.5-fold or greater, such as 2-fold or greater, such as 2.5-fold or greater, such as 3-fold or greater, such as 5-fold or greater and including increasing harvested crop by 10-fold or greater. For example, the increased harvested crop may range from 1.5-fold to 25-fold, such as from 2-fold to 20-fold, such as from 3-fold to 18-fold and including from 5-fold to 15-fold. In certain instances, where the harvested crop are fruits or nuts, compositions for fertilizing soil provided by the invention may increase the amount of crop produced by 250 pounds per acre or more, such as 500 pounds per acre or more, such as 1000 pounds per acre or more, such as 1500 pounds per acre or more and including by 2000 pounds per acre or more. For example the harvested crop may be increased from 250 pounds to 5000 pounds, such as from 500 pounds to 4500 pounds, such as from 750 pounds to 4000 pounds and including from 1000 pounds to 3000 pounds. Enhanced overall health of the subject plants according to the subject methods may, in certain instances, also be realized by an improvement in the quality of harvested crops (e.g., color, taste, duration of shelf life, etc.) as compared to soil not treated with the subject compositions.

Enhanced overall health of the subject plants may also include increased resistance to detrimental effects of pathogens (bacteria, viruses), pests (e.g., mites, aphids, psyllids, etc.) and chemical toxins (such as herbicides, insecticides, fungicides, miticides and other chemical compounds which exhibit phytotoxicity). As described above, by increased resistance to the detrimental effects of pathogens, pests and chemical toxins is meant that the amount required to result in detrimental effects on the subject plants is greater as compared to plants not treated by the subject methods. For example, the amount of pathogens, pests or chemical toxins required to cause detrimental effects to plants treated by the subject methods may be increased by 10% or more, such as 25% or more, such as 50% or more, such as 75% or more and including by 100% or more as compared to plants not treated by the subject methods. In other instances, the amount of pathogens, pests or chemical toxins required to cause detrimental effects to plants treated by the subject methods may be increased by 1.5-fold or greater, such as 2-fold or greater, such as 2.5-fold or greater, such as 3-fold or greater, such as 5-fold or greater and including by 10-fold or greater as compared to plants not treated by the subject methods.

The subject methods also include remediating soil. As discussed above, the term "remediating" is to refer to reducing the overall negative effect of undesirable organic or inorganic contaminants in the soil on plants such that the plants experience a decreased amount of negative effects by the undesirable organic or inorganic contaminants as compared to plants in soil not treated with the subject composition. The overall negative effect by undesirable organic or inorganic contaminants may be reduced, such as by reducing the overall amount of undesirable organic or inorganic contaminants (i.e., oxidative-reductive reactions) in the soil or by reducing the severity or extent of negative effects of the undesirable organic or inorganic contaminants (i.e., the amount of contaminants remain unchanged but initiate fewer detrimental effects).

As discussed above, the subject compositions are synergistically effective combinations of a cellulose nutrient component, a microbial blend component, a source of nitrogen, a source of phosphorus and exotic micronutrients. As such, methods for fertilizing and remediating soil according embodiments of the present invention produce an effect which is greater than would be achieved by the sum of applying each component, individually. For example, in some instances, the subject methods produce an effect which is greater than would be achieved by the sum of individually applying a composition having a cellulose nutrient component and a composition having a microbial blend component, a source of nitrogen, a source of phosphorus and exotic micronutrients. In other instances, the subject methods produce an effect which is greater than would be achieved by the sum of individually applying a composition having a microbial blend component and a composition having a cellulose nutrient component, a source of nitrogen, a source of phosphorus and exotic micronutrients. In yet other instances, the subject methods produce an effect which is greater than would be achieved by the sum of individually applying a composition having a cellulose nutrient component and a microbial blend component and a composition having a source of nitrogen, a source of phosphorus and exotic micronutrients.

The synergistic effect produced by the subject methods may be realized, in certain embodiments, by increased soil fertilization as compared soil fertilization achieved when applying each component individually. As discussed above, enhanced fertilization may be realized by greater production of some desirable parameter, such as for example the amount of harvestable crop produced. Likewise, the synergistic effect of the subject methods may be realized, in some embodiments, by increased soil remediation as compared to soil remediation by applying each component individually. For example, increased soil remediation may be realized by a reduced overall negative effect of undesirable organic or inorganic contaminants in the soil on plants, such as by reducing the overall amount of undesirable organic or inorganic contaminants in the soil or by reducing the severity or extent of negative effects of the undesirable organic or inorganic contaminants (i.e., the amount of contaminants remain unchanged but initiate fewer detrimental effects).

In embodiments of the invention, methods include contacting the soil with one or more of the compositions as described above. By contacting is meant that an amount of the composition is placed onto the surface or incorporated into the soil, such as by using conventional agricultural equipment, mixers, blenders or compost tumblers. The composition may be contacted with soil by any convenient protocol. In some embodiments, compositions are contacted by aerial application. Aerial application may include, but is not limited to spraying, dropping and otherwise applying the subject compositions by agricultural aircraft, gliders, helicopters, ultralights, biplanes, remote control airplanes, as well as motorized, mechanically or electrically powered sprayers or dusters supported by an elevated apparatus (e.g., towers, hydraulic lifts, cranes or support columns). In other embodiments, compositions may be contacted with soil on the ground using motorized, mechanically or electrically powered applicators, such as a tractor or other agricultural vehicle equipped with a sprayer or by hand-held sprayers and the like. Compositions may alternatively be manually applied (i.e., by hand). In yet other embodiments, the subject composition is contacted with the soil by removing the soil from the ground and mixing the removed soil with one or more compositions of interest, such as in an industrial mixer, blender or tumbler. In these embodiments, the soil-fertilizer composition mixture can subsequently reincorporated back to the original location of the soil or some other location.

The amount of the composition employed during any single application may vary depending on the condition of the soil, geographical area and environmental conditions (e.g., wind conditions, precipitation, etc.). Any amount may be applied so long as the amount is sufficient to treat the soil as desired. In some embodiments, the amount applied per acre may range from about 0.01 to 10 pounds per acre, such as 0.05 to 9 pounds per acre, such as 0.1 to 8 pounds per acre, such as 0.5 to 7 pounds per acre, such as 1 to 6 pounds per acre and including 2 to 5 pounds per acre. Depending on the type of condition of the soil, geographical area, environmental conditions, the subject compositions may be applied periodically (i.e., in predetermined time intervals). As such, the composition may be applied daily, weekly, every two weeks, monthly etc. In certain embodiments, the subject compositions are applied after each harvest. Alternatively, the subject compositions may be simply applied as needed, where fertilization or soil remediation is determined to be necessary or desired as by a trained agriculturalist or apiculturist.

Methods may include a single application of the subject compositions or may include multiple application intervals. By "multiple application intervals" is meant more than a single application of the composition, i.e., one or more subsequent application of the composition is performed after the first application. In practicing methods of the invention, protocols may include two or more application intervals, such as three or more application intervals, such as four or more application intervals and including five or more application intervals.

The duration between application intervals may vary depending on the size of soil plot, geographical location, environmental conditions, the condition of the soil, detrimental compounds (e.g., toxins, hazardous waste, parasitic species) found in the soil, etc. In certain instances, the duration between application intervals may be predetermined and follow at regular intervals. For example, the time between application intervals may be 1 hour or longer, such as 2 hours or longer, such as 5 hours or longer, such as 10 hours or longer, such as 12 hours or longer, such as 24 hours or longer, such as 48 hours or longer, such as 72 hours or longer, such as 96 hours or longer and including 168 hours or longer. Alternatively, the time between application intervals may be on demand, where one or more subsequent applications is performed based on need determined by a trained agriculturalist or apiculturist.

Methods of the invention according to certain embodiments also include determining and assessing the make-up of the soil. Determining the makeup of the soil refers to the analysis of one or more of the properties and/or the components present in the soil. Determining the makeup of the soil may include, but is not limited to, determining the microbial composition, plant pathogen composition, fungal composition, organic matter composition, the metal composition, salt composition, ionic composition, organometallic composition and pH. Any convenient protocol can be employed to determine the makeup of the soil of the subject plants. In some embodiments, prior to analysis, a sample of the soil may be obtained and filtered (e.g., by vacuum filtration) to separate the solid components from any liquid components. Suitable protocols for analyzing soil may include, but are not limited to the use of nuclear magnetic spectroscopy, UV-vis spectroscopy, infrared spectroscopy, high performance liquid chromatography, liquid chromatography-mass spectrometry, inductively coupled plasma emission spectrometry, inductively coupled plasma mass spectrometry, ion chromatography, X-ray diffraction, gas chromatography, gas chromatography-mass spectrometry, flow-injection analysis, scintillation counting, acidimetric titration, and flame emission spectrometry.

In some embodiments, determining and assessing the make-up of the soil includes evaluating the microbial activity of the soil. The microbial activity of the soil may be evaluated using any convenient protocol, such as for example the Formozan test. In certain instances, the Formozan test parameters include:

Sterile soil: 10-50
Little Activity: 60-150
Mild Activity: 200-600
High Activity: 750-1500
Superior Activity: >2000

Where desired, the microbial activity may be increased, such as for example by 2-fold or greater, such as by 3-fold or greater, such as by 4-fold or greater, such as by 5-fold or greater, such as by 10-fold or greater, such as by 50-fold or greater and including increasing microbial activity of the soil by 100-fold or greater. For example, the microbial activity may be increased by from 2-fold to 100-fold, such as from 5-fold to 50-fold and including increasing microbial activity by from 10-fold to 25-fold. Where microbial activity is measured according to the Formozan parameters summarized above, increasing microbial activity may include raising the Formozan test result of the soil to 750 or greater, such as 1000 or greater, such as 1500 or greater, such as 2000 or greater and including 2500 or greater. For example, in certain instances, the microbial activity is raised to about 3000 or less, such as to about 2500 or less, such as to about 2250 or less and including to about 2000 or less.

Determining and assessing the make-up of the soil may be performed at any time as desired. For example, determining and assessing the make-up the soil may be performed at predetermined intervals such as every day, every week, every two weeks, every month, etc. Alternatively, determining and assessing the make-up of the soil may be performed in conjunction with methods for applying the subject compositions as described above. For example, the soil may be sampled between intervals during a multiple application interval. The make-up of the soil may be evaluated 1 hour or later after applying the subject compositions, such as 2 hours or later, such as 3 hours or later, such as 5 hours or later, such as 10 hours or later, such as 12 hours or later, such as 24 hours or later, such as 48 hours or later and including 72 hours or later after applying the subject compositions. In some embodiments, the make-up of the soil is evaluated before treating the soil with the subject compositions. In other embodiments, the make-up of the soil is evaluated after treating the soil with the subject compositions. In yet other embodiments, the make-up of the soil is evaluated both before and after treating the soil with the subject compositions.

In certain embodiments, methods include determining that soil is in need of remediation. Determining that soil is in need of remediation may be performed by any convenient protocol, such as determined by a trained professional agriculturalist or apiculturist. In practicing methods of the invention according to certain embodiments, determining whether soil is in need of remediation may include assessing the microbial activity of the soil and evaluating by a human (either alone or with the assistance of a computer, if using a computer-automated program initially set up under human direction) whether the soil would benefit from increase microbial activity in the soil. In other embodiments, determining whether soil is in need of remediation includes assessing the nutrient content of the soil and identifying if the soil requires or would benefit from supplementing one or more nutrients. In yet other embodiments, determining whether soil is in need of remediation includes assessing for the presence of detrimental species in the soils, such as pathogens (pathogenic bacteria, viruses), plant parasitic species (e.g., parasitic nematodes), pests (e.g., mites, aphids, psyllids, etc.) and chemical toxins (such as herbicides, insecticides, fungicides, miticides and other chemical compounds which exhibit phytotoxicity).

In some instances, soil may be determined to be in need of treatment by the subject methods where the soil exhibits microbial activity according to the Formazan test which is 600 or less, such as 500 or less, such as 400 or less, such as 300 or less, such as 250 or less, such as 100 or less and including where the soil exhibits microbial activity according to the Formazan test which is 50 or less. Any convenient Formazan test may be employed, such as the one described in ISO 16072:2002 and titled: Soil quality—Laboratory methods for determination of microbial soil respiration."

In other instances, soil may be determined to be in need of treatment by the subject methods where the soil includes the presence detrimental species above a predetermined threshold. For example, the soil may be determined to be in need of remediation where the concentration of one or more chemical toxins is above a predetermined threshold or where the population of pathogenic or parasitic species is above a predetermined threshold, as determined by a trained professional agriculturalist or qualified apiculturist In yet other instances, soil may be determined to be in need of treatment by the subject methods where plants in the soil have shown a 5% or greater decrease in crop production as compared to a suitable control (e.g., previous seasons production), such as a 10% or greater decrease in crop production, such as a 15% or greater decrease in crop production, such as a 20% or greater decrease in crop production and including a 25% or greater decrease in crop production as compared to a suitable control.

In still other instances, the soil may be determined to be in need of treatment according the subject methods where plants in the soil have shown a crop production per area (e.g., pounds of fruits, nuts, vegetables, etc. per acre) which is below a predetermined threshold. For example, the soil may be determined to be in need of treatment by the subject methods where the crop production per area is 2% or greater below a predetermined threshold, such as 3% or greater below, such as 4% or greater below, such as 5% or greater below and including 10% or greater below a predetermined threshold.

Methods for Preparing Pelletized Fertilizer Compositions

As summarized above, aspects of the invention also include methods for preparing pelletized fertilizer compositions. In certain embodiments, methods for preparing the subject pelletized fertilizer compositions may be characterized by a first process of producing a fertilizer pellet precursor composition, which includes a cellulose nutrient component, microbial blend component, source of nitrogen, source of phosphorus, exotic micronutrients and a binder and then a second process of producing the final fertilizer pellets from the fertilizer pellet precursor composition.

In some embodiments, methods for preparing pelletized fertilizer compositions of interest include combining a cellulose nutrient component, a microbial blend component, a source of nitrogen, a source of phosphorus, exotic micronutrients and a binder to produce a fertilizer pellet precursor composition and pelletizing the precursor composition to produce one or more fertilizer pellets.

In other embodiments, methods include combining a cellulose nutrient component, microbial blend component, a source of nitrogen, a source of phosphorus, exotic micronutrient and a binder and one or more of a carbon skeleton energy component, macronutrients, micronutrients, vitamin cofactors, a complexing agent, an ionophore, and an activator composition to produce an fertilizer pellet precursor composition and pelletizing the precursor composition to produce one or more fertilizer composition pellets.

In yet other embodiments, methods include combining a cellulose nutrient component, microbial blend component, a source of nitrogen, a source of phosphorus, exotic micronutrient, wood and a binder to produce an fertilizer pellet precursor composition and pelletizing the precursor composition to produce one or more fertilizer composition pellets.

In still other embodiments, methods include combining a cellulose nutrient component, microbial blend component, a source of nitrogen, a source of phosphorus, exotic micronutrient, wood and a binder and one or more of a carbon skeleton energy component, macronutrients, micronutrients, vitamin cofactors, a complexing agent, fulvic acid, an ionophore, and an activator composition to produce an fertilizer pellet precursor composition and pelletizing the precursor composition to produce one or more fertilizer composition pellets.

The components of the fertilizer pellet precursor composition may be mixed together by any convenient mixing protocol, such as but not limited to planetary mixers, Patterson-Kelley blender, hand mixers, standup mixers, inline mixers, powder liquid mixers, batch mixers, kneaders, agitator drives, impellers, hydrofoil mixers, aerators, among other mixing protocols.

In some embodiments, all of the components of the fertilizer pellet precursor composition are added to the mixer simultaneously. In other embodiments, each component may be added to the mixer sequentially. One or more components may be mixed concurrently while being added to the mixer or all of the components are first added to the mixer and then the entire fertilizer pellet precursor composition is mixed.

In some embodiments, methods include drying the cellulose nutrient component prior to combining with the other components to produce the fertilizer pellet precursor composition. By "drying" is meant that water is removed from the cellulose nutrient component such that the dried cellulose nutrient component contains 5% w/w water or less, such as 3% w/w water or less, such as 2% w/w water or less, such as 1% w/w water or less, such as 0.5% w/w water or less, such as 0.1% w/w water or less, such as 0.05% w/w water or less, such as 0.01% w/w water or less, such as 0.005% w/w water or less and including 0.001% w/w water or less. The cellulose nutrient component may be dried using any convenient protocol. For example, the cellulose nutrient component may be dried under elevated temperatures, such as in an oven or furnace under atmospheric or reduced pressure. For instance, the temperature may range from 50° C. to 250° C., such as 55° C. to 200° C., such as 60° C. to 150° C. and including 65° C. to 100° C. In other embodiments, drying may also be achieved by spray drying the cellulose nutrient component, where water is removed by a gaseous stream at an elevated temperature. In certain instances, cellulose nutrient component is air-dried by blowing air (e.g., room temperature or heated air) over the cellulose nutrient component. In these instances, the temperature employed during air-drying may vary, so long as the temperature is sufficient to dry the cellulose nutrient component without altering or damaging the cellulose nutrient compound. In yet other embodiments, the cellulose nutrient component may be sun-dried by maintaining the harvested cellulose nutrient component under sunlight.

In some embodiments, the particle size of the cellulose nutrient component is reduced before mixing the components of the fertilizer pellet precursor composition together. In certain instances, the cellulose nutrient component is processed into a powder. The particle size of the cellulose nutrient component may be reduced by any convenient protocol and may include but is not limited to lump breakers, hammermills, fine grinders, classifier mills or sifters, among other particle size reduction protocols. In certain embodiments, to reduce the particle size, the cellulose nutrient component is passed through a mesh screen. Depending on the particle size desired, the mesh screen may vary. In some embodiments, the mesh screen is a 40 mesh screen or smaller, such as a 45 mesh screen or smaller, such as a 50 mesh screen or smaller, such as a 55 mesh screen or smaller and including a 60 mesh screen or smaller.

The components of the fertilizer composition are mixed together for an amount of time sufficient to incorporate each component and to produce a homogenous mixture. For example, methods may include mixing for 1 minute or more, such as 2 minutes or more, such as 3 minutes or more, such as 5 minutes or more, such as 10 minutes or more, and including 15 minutes or more.

In certain instances, the fertilizer pellet precursor composition may be milled to reduce or homogenize the particle size of the precursor composition. The fertilizer pellet precursor composition may be milled by any convenient milling protocol, for example, round impellers, axial flow impellers, radial flow impellers, ball mill, rod mill, autogenous mill, pebble mill, grinding rolls, burrstone mills, semi-autogenous mill, vibratory mill or roller mill, among other protocols.

After incorporating all of the desired components, fertilizer pellets may be produced from the fertilizer pellet precursor composition by any convenient powder compression protocol, such as by pelletization, tableting, among others. In some embodiments, fertilizer pellets of interest are produced by tableting the fertilizer peller precursor composition in a manner sufficient to produce a pellet having a hardness ranging from 2 to 25 kP (kilopond) per $cm^2$, such as 3 to 22 kP per $cm^2$, such as 5 to 20 kP per $cm^2$, such as 5 to 15 kP per $cm^2$, such as 5 to 12 kP per $cm^2$ and including such as 5 to 10 kP per $cm^2$. The hardness of pelleted fertilizer compositions may be determined using any convenient protocol, including but not limited to a Monsanto hardness tester, Strong-Cobb hardness tester, VarianVK hardness tester, Pfizer hardness tester, Erwecka hardness tester or Schleuniger hardness tester, among other hardness testers.

The subject fertilizer pellets may be pelletized into any shape as desired, such as in the shape of a circle, oval, half-circle, crescent, star, square, triangle, rhomboid, pentagon, hexagon, heptagon, octagon, rectangle or other suitable polygon or in the shape of a sphere, tablet, capsule, cube, cone, half sphere, star, triangular prism, rectangular prism, hexagonal prism or other suitable polyhedron. In certain embodiments, the fertilizer pellet precursor composition is pelletized into spheres. In other embodiments, the fertilizer pellet precursor composition is pelletized into the shape of cylinders.

The subject fertilizer pellet precursor composition may be pelletized into any size as desired, such as having a surface area which is 0.01 cm$^2$ or more, such as 0.05 cm$^2$ or more, such as 0.1 cm$^2$ or more, such as 0.5 cm$^2$ or more, such as 1 cm$^2$ or more, such as 2.5 cm$^2$ or more, such as 5 cm$^2$ or more, such as 7.5 cm$^2$ or more, such as 10 cm$^2$ or more, such as 12.5 cm$^2$ or more, such as 25 cm$^2$ or more and including 50 cm$^2$ or more. For example, the fertilizer pellet precursor composition may be pelletized to have a surface area that ranges from 0.01 cm$^2$ to 100 cm$^2$, such as 0.05 cm$^2$ to 90 cm$^2$, such as 0.1 cm$^2$ to 75 cm$^2$, such as 0.5 cm$^2$ to 50 cm$^2$, such as 0.75 cm$^2$ to 25 cm$^2$ and including 1 cm$^2$ to 10 cm$^2$. The fertilizer pellet precursor composition may be pelletized to have a volume that is 0.01 cm$^3$ or more, such as 0.05 cm$^3$ or more, such as 0.1 cm$^3$ or more, such as 0.5 cm$^3$ or more, such as 1 cm$^3$ or more, such as 2.5 cm$^3$ or more, such as 5 cm$^3$ or more, such as 7.5 cm$^3$ or more, such as 10 cm$^3$ or more, such as 12.5 cm$^3$ or more, such as 25 cm$^3$ or more and including 50 cm$^3$ or more. For example, the fertilizer pellet precursor composition may be pelletized to have a volume that ranges from 0.01 cm$^3$ to 100 cm$^3$, such as 0.05 cm$^3$ to 90 cm$^3$, such as 0.1 cm$^3$ to 75 cm$^3$, such as 0.5 cm$^3$ to 50 cm$^3$, such as 0.75 cm$^3$ to 25 cm$^3$ and including 1 cm$^3$ to 10 cm$^3$.

The temperature in preparing the subject pelletized fertilizer compositions may vary depending on the amount of components added as well as the type of microbes in the microbial blend component and may range from 10° C. to 75° C., such as 15° C. to 70° C., such as 20° C. to 65° C. and including 25° C. to 60° C.

Kits

Also provided are kits, where kits at least include one or more, e.g., a plurality of the subject compositions, as described above. In certain embodiments, the subject compositions in the kits may be provided in a package. For example, the compositions of the kits may be presented in individual pouches, bottles, or analogous containers, to preserve the compositions until use. For example, one form of suitable packaging is an air-tight container, air-tight bag, re-sealable water-tight/air-tight container, water-impermeable plastics material (e.g., polyvinylchloride), etc.

In some embodiments, kits may include a separate amount of each component of the subject compositions (e.g., cellulose nutrient component, microbial blend component, source of nitrogen, source of phosphorus, exotic micronutrients, carbon skeleton compound, activator composition, micronutrients, binder, wood, resin, etc.) where the user can mix each component separately in proportions desired, prior to application. In these embodiments, kits may further include one or more containers for mixing the subject compositions as well as a measuring device for portioning out each component, as desired.

In certain instances, kits of interest include an amount of a cellulose nutrient component, a microbial blend component, a source of nitrogen, a source of phosphorus, exotic micronutrients, a binder and instructions for mixing and pelletizing the cellulose nutrient component, microbial blend component, source of nitrogen, source of phosphorus, exotic micronutrients and binder to produce a plurality of fertilizer pellets.

In other instances, kits of interest include an amount of a cellulose nutrient component, a microbial blend component, a source of nitrogen, a source of phosphorus, exotic micronutrients, a binder, an activator composition and instructions for mixing and pelletizing the cellulose nutrient component, microbial blend component, source of nitrogen, source of phosphorus, exotic micronutrients, binder and activator composition to produce a plurality of fertilizer pellets.

In yet other instances, kits of interest include an amount of a cellulose nutrient component, a microbial blend component, a source of nitrogen, a source of phosphorus, exotic micronutrients, a binder, an activator composition, wood and instructions for mixing and pelletizing the cellulose nutrient component, microbial blend component, source of nitrogen, source of phosphorus, exotic micronutrients, binder, activator composition and wood to produce a plurality of fertilizer pellets.

As described above, compositions of interest may in certain instances, be dry compositions. Accordingly, kits provided herein may further include a desiccant compound which absorbs atmospheric moisture during storage of the subject compositions. In embodiments, the desiccant may be any convenient hygroscopic compound which induces or sustains the moisture content of the subject compositions during storage such that the water content of the subject compositions remains 1% w/w water or less, such as 0.5% w/w water or less, such as 0.25% w/w water or less, such as 0.1% w/w water or less, such as 0.05% w/w water or less, such as 0.01% w/w water or less and including 0.001% w/w water or less. The desiccant may be contained in a separate package so that it does not contaminate the subject compositions, for example in a mesh bag, opened container, or air/water permeable polymeric or non-polymeric package. Desiccants of interest may include, but are not limited to silica gel, propylene glycol, hexylene glycol, butylene glycol, glycerol triacetate, vinyl alcohol, neoagarobiose, glycerol, sorbitol, xylitol, maltitol, polydextrose, quillaia, lactic acid, urea, glycerin, aloe vera gel, activated alumina, aerogel, benzophenone, bentonite clay, calcium chloride, calcium sulfate, colbalt(II) chloride, copper(II) sulfate, lithium chloride, lithium bromide, magnesium sulfate, magnesium perchlorate, molecular sieves, potassium carbonate, sodium, sodium chlorate, sodium chloride, sodium hydroxide, sodium sulfate, sucrose and phosphorus pentoxide, among other desiccants.

Kits may further include components for practicing the subject methods, such as devices for applying the compositions to the soil (e.g., sprayers or applicators), cartridges having a loaded predetermined amount of the subject compositions, measuring cups or devices for portioning desired amounts for application.

In addition, kits may also include instructions for how to use the subject compositions, where the instructions may include information about to how to apply the compositions to the soil, application interval schedules, and record keeping devices for executing an application interval regimen. The instructions are recorded on a suitable recording medium. For example, the instructions may be printed on a substrate, such as paper or plastic, etc. As such, the instructions may be present in the kits as a package insert, in the labeling of the container of the kit or components thereof (i.e. associated with the packaging or subpackaging) etc. In other embodiments, the instructions are present as an electronic storage data file present on a suitable computer readable storage medium, e.g., portable flash drive, CD-ROM, diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, the protocol for obtaining the instructions may be recorded on a suitable substrate.

Utility

The aqueous compositions of the subject invention find use in a variety of different applications, where such applications include: the control of soil borne pests and pathogens; the improvement of water filtration; the improvement in mineral release; the enhancement in the water holding capacity of soil; the mellowing of soil textural qualities; the enhancement of the decomposition of plant tissues and accelerated degradation of potentially toxic chemicals and/or allelopathic chemicals; the improvement of root mass in plants grown in treated soil; and the like.

The subject methods, i.e., soil application of the composition, may result in an enhancement of growth of a plant in the treated soil, as compared to a plant in untreated soil. By enhancement of growth is meant that over a set period of time, the plant in the treated soil attains a higher total mass than the plant in the untreated soil. The amount of enhancement will typically be at least about 5%, usually at least about 10% and more usually at least about 25%, where in many embodiments the amount of enhancement may be 50% or greater. In many embodiments, the amount of enhancement will be at least about 100%.

Embodiments of the invention may also result in enhancement of crop yield, e.g., by 5-fold or more, 10-fold or more, 15-fold or more, 20-fold or more, etc, where the amount of enhancement may be 25% or greater, e.g., 50% or greater.

A variety of different soil borne pests may be controlled with the subject compositions. Such pests include: plant parasitic nematodes, *phylloxera*, grubs, and the like. By controlled is meant that the pest population in the soil is reduced, generally by at least about 5%, usually at least about 25% and more usually at least about 50%. As such, the invention provides methods and compositions for at least reducing, if not substantially eliminating, the population of soil borne pests in soil.

Similarly, the subject methods and compositions provide means for reducing the amount of pathogen present in soil. Pathogens that can be targeted with the subject methods include: pathogenic fungi, actinomycetes, bacteria, viruses, and the like. The subject methods result in a reduction of at least about 5%, usually at least about 25%, and more usually at least about 50% of the amount of pathogen in the soil.

Also provided by the subject invention are methods and compositions for increasing indigenous soil microbe populations. Beneficial microbes whose population may be increased by the subject invention include: bacteria, fungi, actinomycetes, various free-living invertebrates, and the like. Applying the composition to the soil according to the subject methods results in at least a 2-fold increase, usually at least about a 20-fold increase and more usually at least about 40-fold increase in the microbe population in the treated soil.

The subject methods and compositions can also be used to improve water filtration through the soil. Water filtration may be improved by at least about 1.5-fold, usually at least about 2.5× and more usually at least about 4.5-fold.

Soil mineral release can also be enhanced using the subject methods and compositions. Mineral release, e.g. the release of minerals such as calcium, potassium and phosphorous, can be improved by at least about 1.5-fold, usually at least about 3.0-fold and more usually at least about 5.0-fold as compared to that observed in control soil.

The subject methods and compositions can be used to increase the root mass of plants grown in the treated soil. Generally, the subject methods result in an increase in root mass of at least about 1.5-fold, usually at least about 2.0-fold and more usually at least about 4.0-fold as compared to control plants, i.e. plants grown in untreated but otherwise substantially identical soil.

The following experiments are offered by way of illustration and not by way of limitation.

EXPERIMENTAL

Example 1

Reduction in $NO_3$ Leaching from Soil

Method:
Five PVC pipes (3' long, schedule 80) were used to simulate a column of soil. Each column was fitted with a valve at the bottom. Fine, washed river sand was used as the medium (sterilized, 40-mesh). Following are the treatments:
Control—Sand only
Pellets A: Rice Hulls–mixed @10% v/v
Pellets B: Rice Hulls 75%, Hardwood 25%–mixed @10% v/v
Pellets C: Rice Hulls+Hardwood+microbes+activator composition–mixed @10% v/v Sand was placed into the column within 5" of the top to accommodate addition of liquid. Each of the pellet treatments (b-d) were mixed homogeneously with the same volume of sand as for treatment 'a'. The columns were placed vertically in a rack. Sterile tap water was run through each column to runoff to prewet the sand and the approximate volume required to wet the column was noted. Seventy two hours (96 hrs) later each column received a volume of nitrate solution (0.60 mM $Ca(NO3)2$, equivalent to ~95 ppm solution of NO3). The volume used was equivalent to the volume noted to wet the entire column. The columns were incubated for 96 hours. At the end of the incubation period sterile tap water (saturation volume+15%) was gently passed through each column and the runoff collected in Erlenmeyer Flasks. The runoff from each treatment was evaluated to determine if the pellet treatments reduced the potential for NO3 leaching. The tests were repeated 5 times. Each test started with clean, washed PVC tubes and new sand and pellets (simulating 5 replications per treatment).
Results:

TABLE 1

| Treatment | Trial 1 | Trial 2 | Trial 3 | Trial 4 | Trial 5 | Mean |
|---|---|---|---|---|---|---|
| Control | 36 | 32 | 31 | 38 | 29 | 33 c |
| Pellets A | 8 | 6 | 9 | 6 | 5 | 7 b |
| Pellets B | 10 | 9 | 12 | 10 | 10 | 10 b |
| Pellets C | 0 | 0 | 0 | 0 | 0 | 0 a | ppm [$NO_3$] In Leachate

As shown in Table 1, the control, pellets A and pellets B allowed nitrate to leach through the column. However, the treatment pellets C having rice hulls, hardwood, microbes and activator composition held onto the nitrate and curtailed leaching through the column.

Example 2

Fertilizer pellets including rice hulls as the cellulose nutrient component were made up having 25% hardwood, microbes and activator. The soil to be treated was previously ripped and prepared to seedbed quality. The soil beds were listed and fitted with buried drip. Into each bed was delivered 2 tons/acre of the pelleted fertilizer composition with activator and microbial blend.

Activator composition (e.g., Tilth, described above) was applied at 40 gallons/acre and the soil allowed to activate for 10 continuous days. The plot also received 1 gallons/acre of microbial blend composition (e.g., Iota, described above) The soil moisture was maintained at 80%-85% field capacity. This treatment replaced fumigation. Crop yields and quality were recorded. The plot treated with the subject compositions yielded 1,800 crates and had 82% Restaurant Grade berries and 18% cannery berries. The Control plot yielded 750 crates with 54% Restaurant Grade and 46% cannery berries.

Example 3

Method:

Nitrogen, Phosphorus, Potassium, Sulfur and Calcium were blended into the fertilizer pellet precursor composition which also contained micronutrients, Zn, Fe, Mn and exotic minerals. Equimolar amounts of each nutrient were used as Control A and pellets with just cellulose nutrient pellet were used as Control B. The treatments were made to newly planted bell peppers and continued throughout the season. The yields were monitored for comparison.

Results:

TABLE 2

| Treatment | Trial 1 | Trial 2 | Trial 3 | Trial 4 | Trial 5 | Mean |
|---|---|---|---|---|---|---|
| Control Composition A | 503 | 485 | 481 | 464 | 429 | 472 a |
| Control Composition B | 754 | 710 | 703 | 697 | 676 | 708 b |
| Fertilizer Pellet | 1,503 | 1,550 | 1,610 | 1,634 | 1,675 | 1,594 c |

Yield in Boxes per acre

As shown above, combining of the cellulose nutrient component with other components of the subject fertilizer composition gives a synergistic response that secures more than the additive effects of either treatment alone.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A composition comprising:
   a cellulose nutrient component;
   a microbial blend component;
   a source of nitrogen;
   a source of phosphorus; and
   exotic micronutrients.

2. The composition according to claim 1, wherein the cellulose nutrient component is a manure crop.

3. The composition according to claim 1, wherein the cellulose nutrient component is present in an amount of from 25% w/w to 95% w/w.

4. The composition according to claim 1, wherein the microbial blend composition comprises at least one bacterial species and at least one fungal species.

5. The composition according to claim 4, wherein the microbial blend component comprises at least 5 distinct microbial species.

6. The composition according to claim 1, wherein the microbial blend component comprises microbial species capable of digesting the cellulose nutrient component.

7. The composition according to claim 1, wherein the microbial blend component comprises bacterial or fungal species that are soil-borne pathogen antagonists.

8. The composition according to claim 1, wherein the soil-borne pathogen antagonist is a plant parasitic nematode antagonist.

9. The composition according to claim 8, wherein the plant parasitic nematode antagonist a rhizobacteria.

10. The composition according to claim 1, wherein total concentration of microbial species in the composition is from $1 \times 10^5$ cfu/ml to $1 \times 10^{15}$ cfu/ml.

11. The composition according to claim 1, wherein the exotic micronutrients are present in an amount ranging from 1 to 15% w/w.

12. The composition according to claim 1, wherein the composition further comprises an activator composition.

13. The composition according to claim 1, wherein the composition further comprises wood.

14. The composition according to claim 13, wherein wood is present in the composition in an amount of from 5% w/w to 50% w/w.

15. The composition according to claim 1, wherein the composition further comprises macronutrients and micronutrients.

16. The composition according to claim 15, wherein the micronutrients are present in an amount ranging from 0.01 ppm to 200 ppm w/w.

17. The composition according to claim 1, wherein the composition is pelletized.

18. The composition according to claim 17, wherein the pelletized composition comprises a binder.

19. The composition according to claim 18, wherein the binder is calcium lignosulfate.

20. A method comprising contacting a composition to soil, wherein the composition comprises a cellulose nutrient component, a microbial blend component, a source of nitrogen, a source of phosphorus and exotic micronutrients.

* * * * *